United States Patent
Dalton et al.

(10) Patent No.: US 7,214,693 B2
(45) Date of Patent: May 8, 2007

(54) HETEROCYCLIC SELECTIVE ANDROGEN RECEPTOR MODULATORS AND METHODS OF USE THEREOF

(75) Inventors: James T. Dalton, Upper Arlington, OH (US); Duane D. Miller, Germantown, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 10/683,125

(22) Filed: Oct. 14, 2003

(65) Prior Publication Data

US 2004/0138244 A1     Jul. 15, 2004

Related U.S. Application Data

(60) Provisional application No. 60/418,173, filed on Oct. 15, 2002.

(51) Int. Cl.
*C07D 401/02* (2006.01)
*C07D 213/02* (2006.01)
*A61K 31/44* (2006.01)

(52) U.S. Cl. .................. 514/352; 514/340; 514/341; 514/342; 514/343; 514/345; 546/269.7; 546/271.4; 546/272.7; 546/290; 546/304

(58) Field of Classification Search ............... 546/300, 546/269.7, 271.4, 272.7, 290, 304; 514/345, 514/340, 341, 342, 343, 352
See application file for complete search history.

(56) References Cited

U.S. PATENT DOCUMENTS 6,174,905 B1    1/2001    Suzuki et al.

FOREIGN PATENT DOCUMENTS

WO    WO 02/16310 A1 *  2/2002

OTHER PUBLICATIONS

Matsumoto Alvin M "Hormonal Therapy of Male Hypogonadism" Endocrinology and Metabolism Clinics of North America, 0889-8529/94, 23:857-75 (1994).
Zhou Zong-xun et al. "Specificity of Ligang-Dependent Androgen Receptor Stabilization: Receptor Domain Interactions Influence Ligand Dissociation and Receptor Stability", Molecular Endocrinology, 9:208-18 (1995).
Sundaram Kalyan et al., "7 Alpha-Methyl-Nortestosterone(MENT): The Optimal Androgen For Male Contraception," Ann. Med., 25:199-205 (1993).
Steinberger Emil et al., "Effect of Chronic Administration of Testosterone Enanthate on Sperm Production and Plasma Testosterone, Follicle Stimulating Hormone, and Luteinizing Hormone Levels: A Preliminary Evaluation of a Possible Male Contraceptive", Fertility and Sterility 28:1320-28 (1977).
World Health Organization Task Force on Methods And Regulation of Male Fertility, "Contraceptive Efficacy of Testosterone-Induced Azoospermia and Oligospermia in Normal Men," Fertility and Sterility 65:821-29 (1996).
Wu Frederick C. W. et al, "Effects of Testosterone Enanthate in Normal Men: Experience From a Multicenter Contraceptive Efficacy Study," Fertility and Sterility 65:626-36 (1996).
Sefton Michael V., "Implantable Pumps" CRC Crit. Ref. Biomed. Eng. 14:201 (1987).
Buchwald Henry et al., "Long-Term, continuous intravenous heparin administration by an implantable infusion pump in ambulatory patients with recurrent venous thrombosis" Surgery 88:507 (1980).
Saudek Christopher D. et al., "A Preliminary Trial of the Programmable Implantable Medication System for Insulin Delivery" New England Journal of Medicine, 321:574 (1989).
Goodson J. Max "Dental Applications" Medical Applications of Controlled Release, supra, vol. 2, pp. 115-138 (1984).
Langer Robert "New Method of Drug Delivery" Science 249:1527-1533 (1990).

* cited by examiner

*Primary Examiner*—Zinna N. Davis
(74) *Attorney, Agent, or Firm*—Pearl Cohen Zedek Latzer, LLP; Mark S. Cohen

(57) ABSTRACT

This invention provides a class of androgen receptor targeting agents (ARTA). The agents define a new subclass of compounds, which are selective androgen receptor modulators (SARM). Several of the SARM compounds have been found to have an unexpected androgenic and anabolic activity of a nonsteroidal ligand for the androgen receptor. Other SARM compounds have been found to have an unexpected antiandrogenic activity of a nonsteroidal ligand for the androgen receptor. The SARM compounds, either alone or as a composition, are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of acute and/or chronic muscular wasting conditions; e) preventing and/or treating dry eye conditions; f) oral androgen replacement therapy; g) decreasing the incidence of, halting or causing a regression of prostate cancer; and/or h) inducing apoptosis in a cancer cell.

63 Claims, No Drawings

HETEROCYCLIC SELECTIVE ANDROGEN RECEPTOR MODULATORS AND METHODS OF USE THEREOF

CROSS REFERENCE TO RELATED APPLICATIONS

This application claims the benefit of U.S. Provisional Application Ser. No. 60/418,173, filed Oct. 15, 2002, which is incorporated in its entirety by reference herein.

GOVERNMENT INTEREST STATEMENT

This invention was made in whole or in part with government support under grant number R29 CA068096 awarded by the National Cancer Institute, National Institute of Health, and under grant number R15 HD35329, awarded by the National Institute of Child Health and Human Development, National Institute of Health. The government may have certain rights in the invention.

FIELD OF INVENTION

The present invention relates to a novel class of androgen receptor targeting agents (ARTA), which are selective androgen receptor modulators (SARM). The SARM compounds are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of acute and/or chronic muscular wasting conditions; e) preventing and/or treating dry eye conditions; f) oral androgen replacement therapy; g) decreasing the incidence of, halting or causing a regression of prostate cancer; and/or h) inducing apoptosis in a cancer cell.

BACKGROUND OF THE INVENTION

The androgen receptor ("AR") is a ligand-activated transcriptional regulatory protein that mediates induction of male sexual development and function through its activity with endogenous androgens. Androgens are generally known as the male sex hormones. The androgenic hormones are steroids which are produced in the body by the testes and the cortex of the adrenal gland or can be synthesized in the laboratory. Androgenic steroids play an important role in many physiologic processes, including the development and maintenance of male sexual characteristics such as muscle and bone mass, prostate growth, spermatogenesis, and the male hair pattern (Matsumoto, Endocrinol. Met. Clin. N. Am. 23:857–75 (1994)). The endogenous steroidal androgens include testosterone and dihydrotestosterone ("DHT"). Testosterone is the principal steroid secreted by the testes and is the primary circulating androgen found in the plasma of males. Testosterone is converted to DHT by the enzyme 5 alpha-reductase in many peripheral tissues. DHT is thus thought to serve as the intracellular mediator for most androgen actions (Zhou, et al., Molec. Endocrinol. 9:208–18 (1995)). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone (MENT): The Optimal Androgen For Male Contraception," Ann. Med., 25:199–205 (1993) ("Sundaram")). Because the AR is involved in male sexual development and function, the AR is a likely target for effecting male contraception or other forms of hormone replacement therapy.

Worldwide population growth and social awareness of family planning have stimulated a great deal of research in contraception. Contraception is a difficult subject under any circumstance. It is fraught with cultural and social, stigma, religious implications, and, most certainly, significant health concerns. This situation is only exacerbated when the subject focuses on male contraception. Despite the availability of suitable contraceptive devices, historically, society has looked to women to be responsible for contraceptive decisions and their consequences. Although concern over sexually transmitted diseases has made men more aware of the need to develop safe and responsible sexual habits, women still often bear the brunt of contraceptive choice. Women have a number of choices, from temporary mechanical devices such as sponges and diaphragms to temporary chemical devices such as spermicides. Women also have at their disposal more permanent options, such as physical devices including IUDs and cervical caps as well as more permanent chemical treatments such as birth control pills and subcutaneous implants. However, to date, the only options available for men include the use of condoms and vasectomy. Condom use, however is not favored by many men because of the reduced sexual sensitivity, the interruption in sexual spontaneity, and the significant possibility of pregnancy caused by breakage or misuse. Vasectomies are also not favored. If more convenient methods of birth control were available to men, particularly long-term methods which require no preparative activity immediately prior to a sexual act, such methods could significantly increase the likelihood that men would take more responsibility for contraception.

Administration of the male sex steroids (e.g., testosterone and its derivatives) has shown particular promise in this regard due to the combined gonadotropin-suppressing and androgen-substituting properties of these compounds (Steinberger et al., "Effect of Chronic Administration of Testosterone Enanthate on Sperm Production and Plasma Testosterone, Follicle Stimulating Hormone, and Luteinizing Hormone Levels: A Preliminary Evaluation of a Possible Male Contraceptive, Fertility and Sterility 28:1320–28 (1977)). Chronic administration of high doses of testosterone completely abolishes sperm production (azoospermia) or reduces it to a very low level (oligospermia). The degree of spermatogenic suppression necessary to produce infertility is not precisely known. However, a recent report by the World Health Organization showed that weekly intramuscular injections of testosterone enanthate result in azoospermia or severe oligospermia (i.e., less than 3 million sperm per ml) and infertility in 98% of men receiving therapy (World Health Organization Task Force on Methods And Regulation of Male Fertility, "Contraceptive Efficacy of Testosterone-Induced Azoospermia and Oligospermia in Normal Men," Fertility and Sterility 65:821–29 (1996)).

A variety of testosterone esters have been developed which are more slowly absorbed after intramuscular injection and thus result in greater androgenic effect. Testosterone enanthate is the most widely used of these esters. While testosterone enanthate has been valuable in terms of establishing the feasibility of hormonal agents for male contraception, it has several drawbacks, including the need for weekly injections and the presence of supraphysiologic peak levels of testosterone immediately following intramuscular injection (Wu, "Effects of Testosterone Enanthate in Normal Men: Experience From a Multicenter Contraceptive Efficacy Study," Fertility and Sterility 65:626–36 (1996)).

Steroidal ligands which bind the AR and act as androgens (e.g. testosterone enanthate) or as antiandrogens (e.g. cyproterone acetate) have been known for many years and are used clinically (Wu 1988). Although nonsteroidal antiandrogens are in clinical use for hormone-dependent prostate cancer, nonsteroidal androgens have not been reported. For this reason, research on male contraceptives has focused solely on steroidal compounds.

Prostate cancer is one of the most frequently occurring cancers among men in the United States, with hundreds of thousands of new cases diagnosed each year. Unfortunately, over sixty percent of newly diagnosed cases of prostate cancer are found to be pathologically advanced, with no cure and a dismal prognosis. One approach to this problem is to find prostate cancer earlier through screening programs and thereby reduce the number of advanced prostate cancer patients. Another strategy, however, is to develop drugs to prevent prostate cancer. One third of all men over 50 years of age have a latent form of prostate cancer that may be activated into the life-threatening clinical prostate cancer form. The frequency of latent prostatic tumors has been shown to increase substantially with each decade of life from the 50s (5.3–14%) to the 90s (40–80%). The number of people with latent prostate cancer is the same across all cultures, ethnic groups, and races, yet the frequency of clinically aggressive cancer is markedly different. This suggests that environmental factors may play a role in activating latent prostate cancer. Thus, the development of treatment and preventative strategies against prostate cancer may have the greatest overall impact both medically and economically against prostate cancer.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spines 250,000 hip and 240,000 wrist fractures annually. Hip fractures are the most serious consequence of osteoporosis, with 5–20% of patients dying within one year, and over 50% of survivors being incapacitated. The elderly are at greatest risk of osteoporosis, and the problem is therefore predicted to increase significantly with the aging of the population. Worldwide fracture incidence is forecasted to increase three-fold over the next 60 years, and one study estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake. However, osteoporosis also occurs frequently in males. It is well established that the bone mineral density of males decrease with age. Decreased amounts of bone mineral content and density correlates with decreased bone strength, and predisposes to fracture. The molecular mechanisms underlying the pleiotropic effects of sex-hormones in non-reproductive tissues are only beginning to be understood, but it is clear that physiologic concentrations of androgens and estrogens play an important role in maintaining bone homeostasis throughout the lifecycle. Consequently, when androgen or estrogen deprivation occurs there is a resultant increase in the rate of bone remodeling that tilts the balance of resorption and formation to the favor of resorption that contributes to the overall loss of bone mass. In males, the natural decline in sex-hormones at maturity (direct decline in androgens as well as lower levels of estrogens derived from peripheral aromatization of androgens) is associated with the frailty of bones. This effect is also observed in males who have been castrated.

Androgen decline in the aging male (ADAM) refers to a progressive decrease in androgen production, common in males after middle age. The syndrome is characterized by alterations in the physical and intellectual domains that correlate with and can be corrected by manipulation of the androgen milieu. ADAM is characterized biochemically by a decrease not only in serum androgen, but also in other hormones, such as growth hormone, melatonin and dehydroepiandrosterone. Clinical manifestations include fatigue, depression, decreased libido, sexual dysfunction, erectile dysfunction, hypogonadism, osteoporosis, hair loss, obesity, sarcopenia, osteopenia, benign prostate hyperplasia, and alterations in mood and cognition.

Androgen Deficiency in Female (ADIF) refers to a variety of hormone-related conditions including, common in females after middle agest. The syndrome is characterized by sexual dysfunction, decreased sexual libido, hypogonadism, sarcopenia, osteopenia, osteoporosis, alterations in cognition and mood, anemia, depression, anemia, hair loss, obesity, endometriosis, breast cancer, uterine cancer and ovarian cancer.

Muscle wasting refers to the progressive loss of muscle mass and/or to the progressive weakening and degeneration of muscles, including the skeletal or voluntary muscles, which control movement, cardiac muscles, which control the heart (cardiomyopathics), and smooth muscles. Chronic muscle wasting is a chronic condition (i.e. persisting over a long period of time) characterized by progressive loss of muscle mass, weakening and degeneration of muscle. The loss of muscle mass that occurs during muscle wasting can be characterized by a muscle protein breakdown or degradation. Protein degradation occurs because of an unusually high rate of protein degradation, an unusually low rate of protein synthesis, or a combination of both. Protein degradation, whether caused by a high degree of protein degradation or a low degree of protein synthesis, leads to a decrease in muscle mass and to muscle wasting. Muscle wasting is associated with chronic, neurological, genetic or infectious pathologies, diseases, illnesses or conditions. These include Muscular Dystrophies such as Duchenne Muscular Dystrophy and Myotonic Dystrophy; Muscle Atrophies such as Post-Polio Muscle Atrophy (PPMA); Cachexias such as Cardiac Cachexia, AIDS Cachexia and Cancer Cachexia, malnutrition, Leprosy, Diabetes, Renal Disease, Chronic Obstructive Pulmonary Disease (COPD), Cancer, end stage Renal failure, Emphysema, Osteomalacia, HW Infection, AIDS, and Cardiomyopathy, In addition, other circumstances and conditions are linked to and can cause muscle wasting. These include chronic lower back pain, advanced age, central nervous system (CNS) injury, peripheral nerve injury, spinal cord injury, chemical injury, central nervous system (CNS) damage, peripheral nerve damage, spinal cord damage, chemical damage, burns, disuse deconditioning that occurs when a limb is immobilized, long term hospitalization due to illness or injury, and alcoholism. Muscle wasting, if left unabated, can have dire health consequences. For example, the changes that occur during muscle wasting can lead to a weakened physical state that is detrimental to an individual's health, resulting in increased susceptibility to infection, poor performance status and susceptibility to injury.

New innovative approaches are urgently needed at both the basic science and clinical levels to develop compounds which are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with ADIF, such as sexual dysfunction, decreased sexual libido, hypogonadism, sarcopenia, osteopenia, osteoporosis, alterations in cognition and moods, depression, anemia, hair loss, obesity, endometriosis, breast cancer, uterine cancer and ovarian cancer; d) treatment and/or prevention of acute and/or chronic muscular wasting conditions; e) preventing and/or treating dry eye conditions; f) oral androgen replacement therapy; and/or g) decreasing the incidence of, halting or causing a regression of prostate cancer.

SUMMARY OF THE INVENTION

This invention provides a class of androgen receptor targeting agents (ARTA). The agents define a new subclass of compounds, which are selective androgen receptor modulators (SARM). Several of the SARM compounds have been found to have an androgenic and anabolic activity of a nonsteroidal ligand for the androgen receptor. Other SARM compounds have been found to have an unexpected antiandrogenic activity of a nonsteroidal ligand for the androgen receptor. The SARM compounds, either alone or as a composition, are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anenia, obesity, sarcopenia, osteopenia, osteoporosis, benign prostate hyperplasia, alterations in mood and cognition and prostate cancer; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of acute and/or chronic muscular wasting conditions; e) preventing and/or treating dry eye conditions; f) oral androgen replacement therapy; g) decreasing the incidence of, halting or causing a regression of prostate cancer; and/or h) inducing apoptosis in a cancer cell.

In one embodiment, the present invention provides a selective androgen receptor modulator (SARM) compound represented by the structure of formula I:

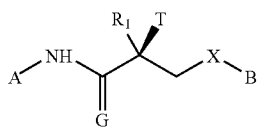

wherein
X is a bond, O, $CH_2$, NH, Se, PR, NO or NR;
G is O or S;
$R_1$ is $CH_3$, $CH_2F$, $CHF_2$, $CF_3$, $CH_2CH_3$, or $CF_2CF_3$;
T is OH, OR, $NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;
A is a ring selected from:

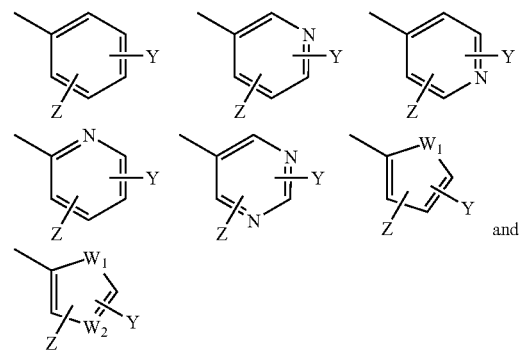

B is a ring selected from:

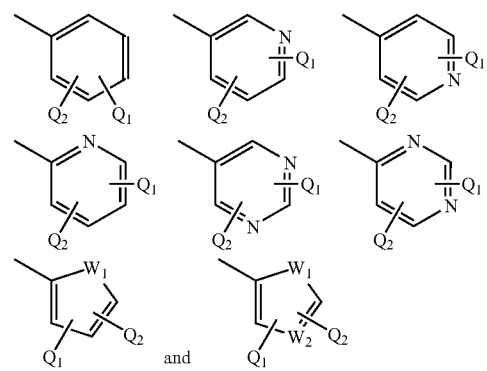

wherein A and B cannot simultaneously be a benzene ring,
Z is $NO_2$, CN, COOH, COR, NHCOR or CONHR;
Y is $CF_3$, F, I, Br, Cl, CN, $(CR)_3$ or $Sn(R)_3$;
$Q_1$ and $Q_2$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR,

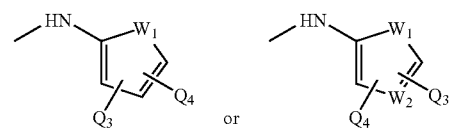

$Q_3$ and $Q_4$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$ or SR;
$W_1$ is O, NH, NR, NO or S; and
$W_2$ is N or NO.

In another embodiment, the present invention provides an analog, isomer, metabolite, derivative, pharmaceutically acceptable salt, pharmaceutical product, hydrate, N-oxide, impurity, prodrug, polymorph or crystal of the compound of formula I, or any combination thereof.

In one embodiment, X in compound I is O. In one embodiment, G in compound I is O. In another embodiment, T in compound I is OH. In another embodiment, R₁ in compound I is CH₃. In another embodiment, Z in compound I is NO₂. In another embodiment, Z in compound I is CN. In another embodiment, Y in compound I is CF₃. In another embodiment, Q₁ in compound I is NHCOCH₃. In another embodiment, Q₁ in compound I is F.

In another embodiment, the compound of formula I is represented by the structure of formula Ia:

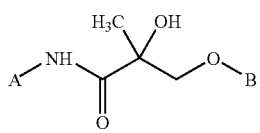

Ia wherein A and B are as defined above for compound I.

In one embodiment, A in compound I is:

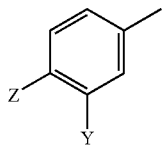

In another embodiment, A in compound I is:

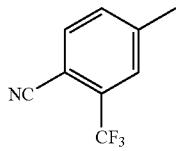

In another embodiment, A in compound I is:

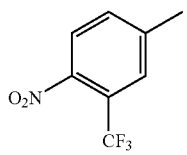

In another embodiment, A in compound I is:

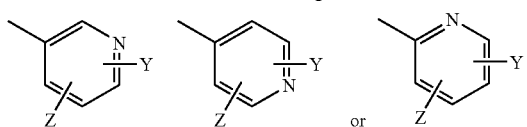

In one embodiment, B in compound I is:

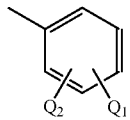

In another embodiment, B in compound I is:

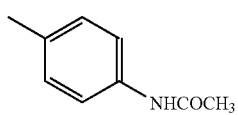

In another embodiment, B in compound I is:

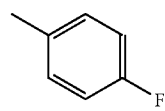

In another embodiment, B in compound I is:

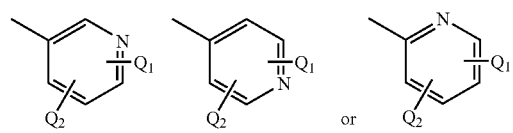

In one embodiment, the present invention further provides a selective androgen receptor modulator (SARM) compound represented by the structure of formula II:

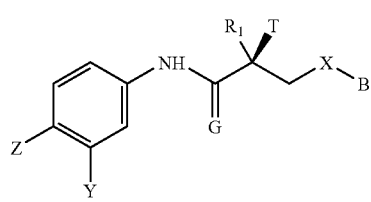

II wherein
X is a bond, O, CH₂, NH, Se, PR, NO or NR;
G is O or S;
R₁ is CH₃, CH₂F, CHF₂, CF₃, CH₂CH₃, or CF₂CF₃;
T is OH, OR, NHCOCH₃, or NHCOR;
R is alkyl, haloalkyl, dihaloalkyl, trihaloalkyl, CH₂F, CHF₂, CF₃, CF₂CF₃; aryl, phenyl, F, Cl, Br, I, alkenyl or OH;
B is a ring selected from:

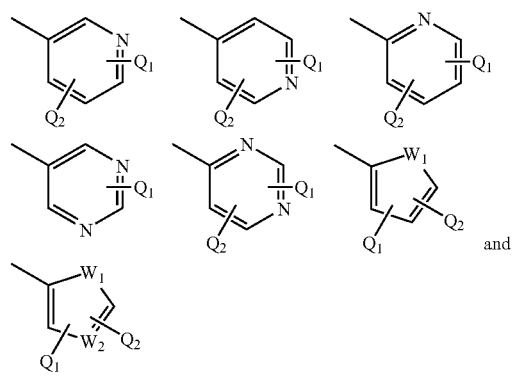

and

Z is NO₂, CN, COOH, COR, NHCOR or CONHR;
Y is CF₃, F, I, Br, Cl, CN, C(R)₃ or Sn(R)₃;
Q₁ and Q₂ are independently of each other a hydrogen, alkyl, F, Cl, Br, I, CF₃, CN, C(R)₃, Sn(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR,

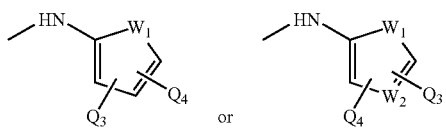

Q₃ and Q₄ are independently of each other a hydrogen, alkyl, F, Cl, Br, I, CF₃, CN, C(R)₃, Sn(R)₃, N(R)₂, NHCOCH₃, NHCOCF₃, NHCOR, NHCONHR, NHCOOR, OCONHR, CONHR, NHCSCH₃, NHCSCF₃, NHCSR NHSO₂CH₃, NHSO₂R, OR, COR, OCOR, OSO₂R, SO₂R or SR;

$W_1$ is O, NH, NR, NO or S; and $W_2$ is N or NO.

In another embodiment, the present invention provides an analog, isomer, metabolite, derivative, pharmaceutically acceptable salt, pharmaceutical product, hydrate, N-oxide, impurity, prodrug, polymorph or crystal of the compound of formula II, or any combination thereof.

In one embodiment, X in compound II is O. In one embodiment, G in compound II is O. In another embodiment, T in compound II is OH. In another embodiment, $R_1$ in compound II is CH₃. In another embodiment, Z in compound II is NO₂. In another embodiment, Z in compound II is CN. In another embodiment, Y in compound II is CF₃. In another embodiment, $Q_1$ in compound II is NHCOCH₃. In another embodiment, $Q_1$ in compound II is F.

In one embodiment, the selective androgen receptor modulator compound is represented by the structure of formula III, wherein B and X are as defined above for formula II.

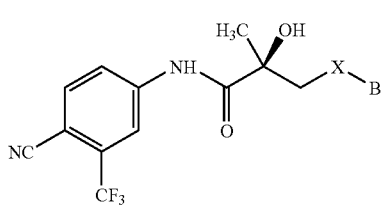

III

In another embodiment, the selective androgen receptor modulator compound is represented by the structure of formula IV, wherein B and X are as defined above for formula II.

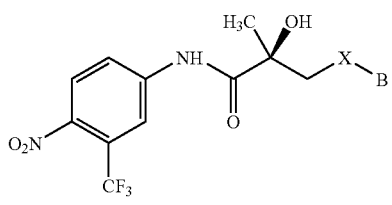

IV

In another embodiment, the selective androgen receptor modulator compound is represented by the structure:

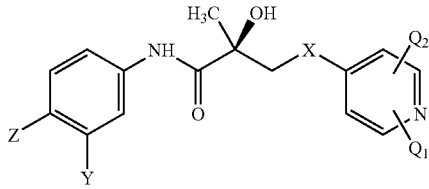

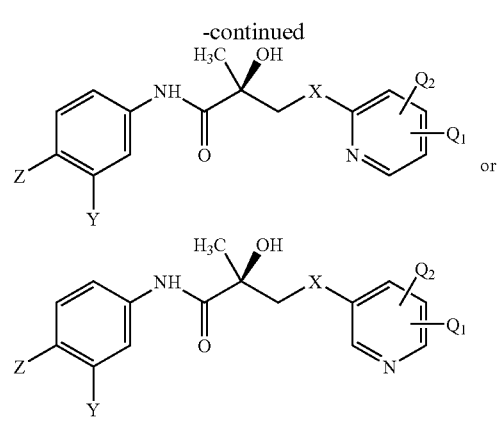

or

In another embodiment, the selective androgen receptor modulator compound is represented by the structure:

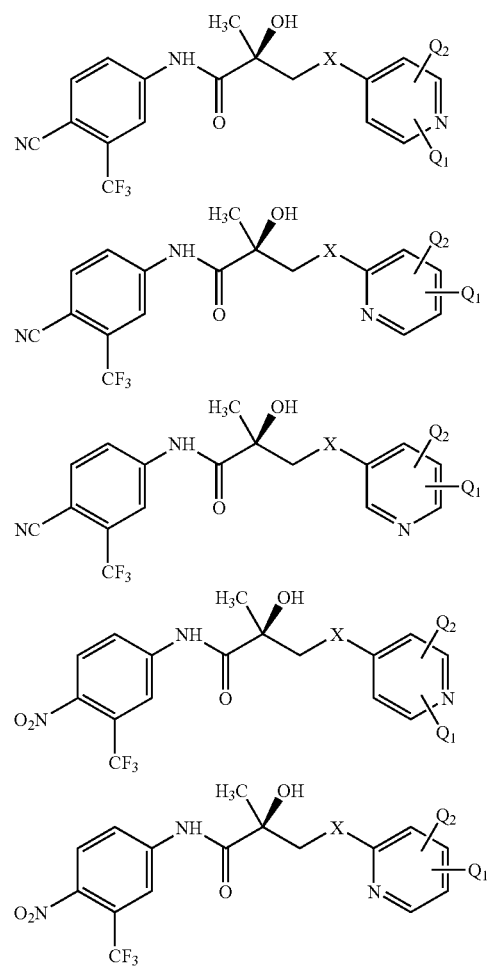

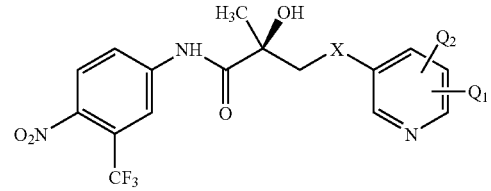

In another embodiment, the selective androgen receptor modulator compound is represented by the structure:

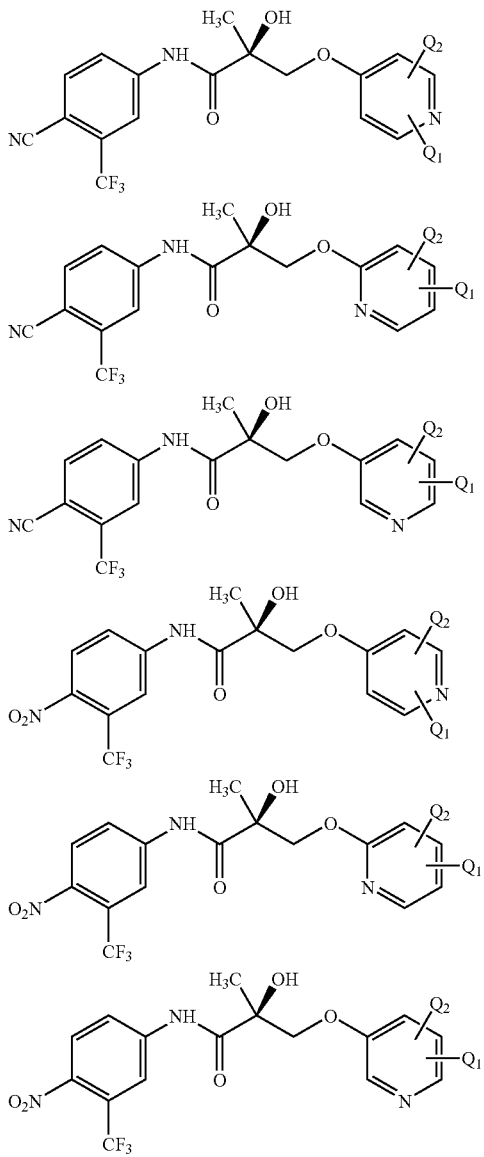

In one embodiment, the present invention further provides a selective androgen receptor modulator (SARM) compound represented by the structure of formula V:

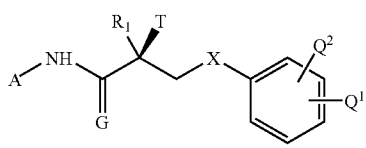

wherein
X is a bond, O, $CH_2$, NH, Se, PR, NO or NR;
G is O or S;
$R_1$ is $CH_3$, $CH_2F$, $CHF_2$, $CF_3$, $CH_2CH_3$, or $CF_2CF_3$;
T is OH, OR, $NHCOCH_3$, or NHCOR;
R is alkyl, haloalkyl, dihaloalkyl, trihaloalkyl, $CH_2F$, $CHF_2$, $CF_3$, $CF_2CF_3$; aryl, phenyl, F, Cl, Br, I, alkenyl or OH;

A is a ring selected from:

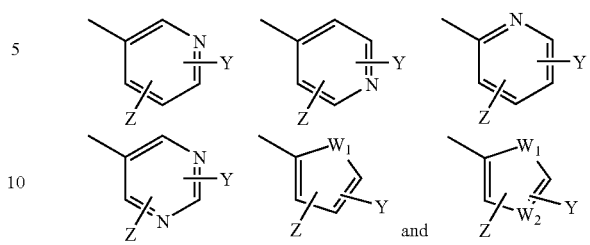

Z is $NO_2$, CN, COOH, COR, NHCOR or CONHR;
Y is $CF_3$, F, I, Br, Cl, CN, $C(R)_3$ or $Sn(R)_3$;
$Q_1$ and $Q_2$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR,

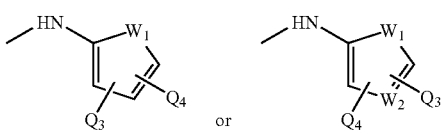

$Q_3$ and $Q_4$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$ or SR;
$W_1$ is O, NH, NR, NO or S; and
$W_2$ is N or NO.

In another embodiment, the present invention provides an analog, isomer, metabolite, derivative, pharmaceutically acceptable salt, pharmaceutical product, hydrate, N-oxide, impurity, prodrug, polymorph or crystal of the compound of formula V, or any combination thereof.

In one embodiment, X in compound V is O. In one embodiment, G in compound V is O. In another embodiment, T in compound V is OH. In another embodiment, $R_1$ in compound V is $CH_3$. In another embodiment, Z in compound V is $NO_2$. In another embodiment, Z in compound V is CN. In another embodiment, Y in compound V is $CF_3$. In another embodiment, $Q_1$ in compound V is $NHCOCH_3$. In another embodiment, $Q_1$ in compound V is F.

In another embodiment, the selective androgen receptor modulator compound of the present invention is represented by the structure of formula VI, wherein A and X are as defined above for formula V.

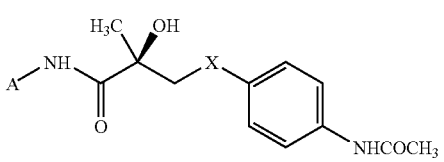

In another embodiment, the selective androgen receptor modulator compound is represented by the structure:

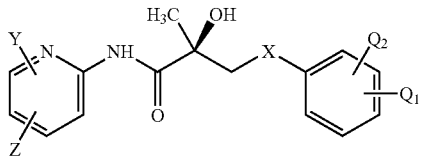

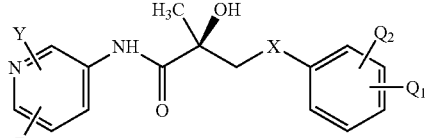

or

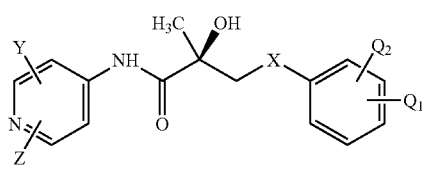

In another embodiment, the selective androgen receptor modulator compound is represented by the structure:

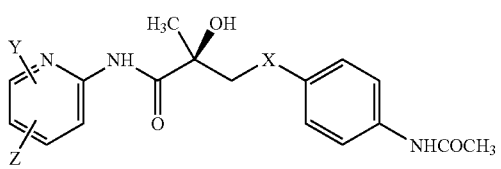

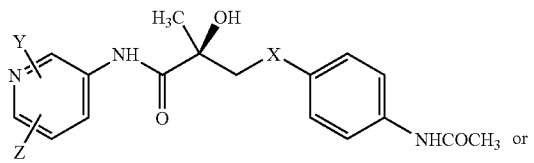

or

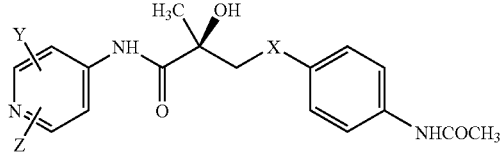

In another embodiment, the selective androgen receptor modulator compound is represented by the structure:

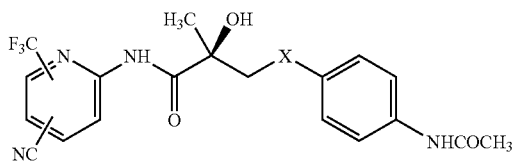

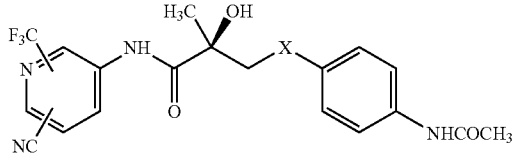

-continued

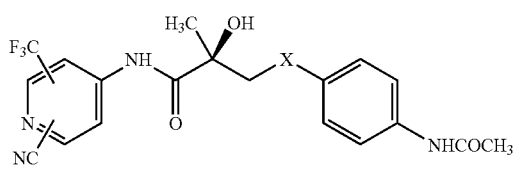

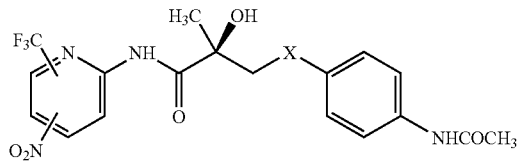

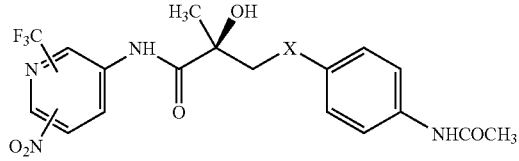

or

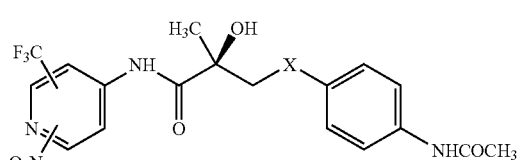

In another embodiment, the selective androgen receptor modulator compound is represented by the structure:

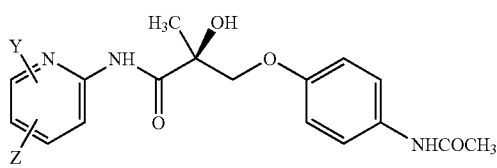

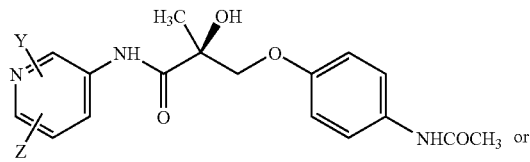

or

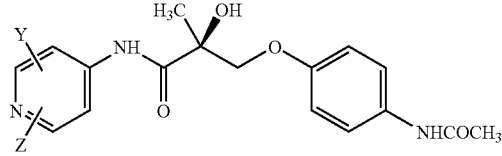

In another embodiment, the selective androgen receptor modulator compound is represented by the structure:

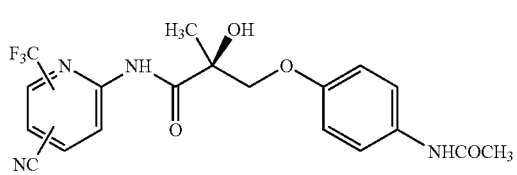

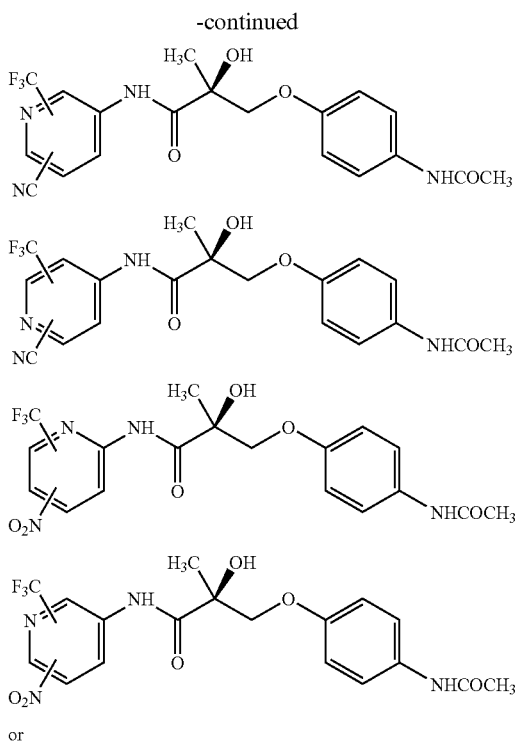

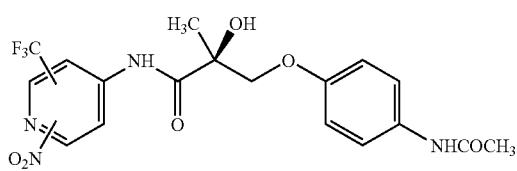

In another embodiment, the selective androgen receptor modulator compound is represented by the structure:

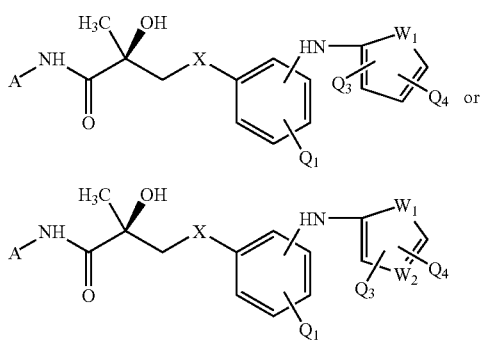

In another embodiment, the selective androgen receptor modulator compound is represented by the structure:

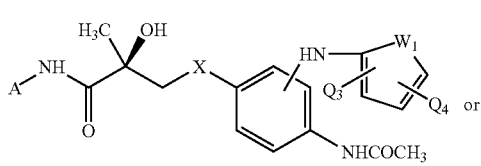

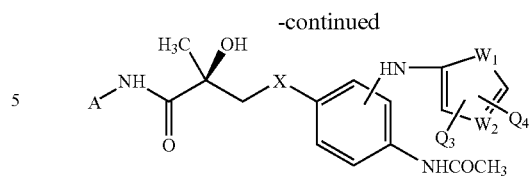

In another embodiment, the selective androgen receptor modulator compound is represented by the structure:

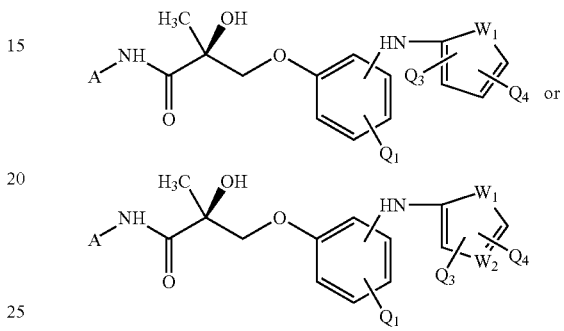

In another embodiment, the selective androgen receptor modulator compound is represented by the structure:

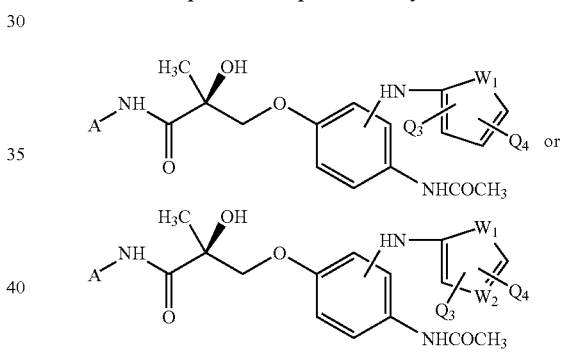

In one embodiment, the present invention provides a composition comprising the selective androgen receptor modulator compound of any of formulas I–VI and/or its analog, derivative, isomer, metabolite, pharmaceutically acceptable salt, pharmaceutical product, hydrate, N-oxide, prodrug, polymorph, crystal or any combination thereof.

In one embodiment, the present invention provides a composition comprising the selective androgen receptor modulator compound of any of formulas I–VI and/or its analog, derivative, isomer, metabolite, pharmaceutically acceptable salt, pharmaceutical product, hydrate, N-oxide, prodrug, polymorph, crystal or any combination thereof; and a suitable carrier or diluent.

In another embodiment, the present invention provides a pharmaceutical composition comprising the selective androgen receptor modulator compound of any of formulas I–VI and/or its analog, derivative, isomer, metabolite, pharmaceutical product, hydrate, or N-oxide or any combination thereof; and a suitable carrier or diluent.

In another embodiment, the present invention provides a method of binding a selective androgen receptor modulator compound to an androgen receptor, comprising the step of contacting the androgen receptor with the selective androgen receptor modulator compound of any of formulas I–VI and/or its analog, derivative, isomer, metabolite, pharmaceutically acceptable salt, pharmaceutical product, hydrate, N-oxide, prodrug, polymorph, crystal or any combination thereof, in an amount effective to bind the selective androgen receptor modulator compound to the androgen receptor.

In another embodiment, the present invention provides a method of suppressing spermatogenesis in a subject comprising contacting an androgen receptor of the subject with the selective androgen receptor modulator compound of any of formulas I–VI and/or its analog, derivative, isomer, metabolite, pharmaceutically acceptable salt, pharmaceutical product, hydrate, N-oxide, prodrug, polymorph, crystal or, any combination thereof, in an amount effective to suppress sperm production.

In another embodiment, the present invention provides a method of contraception in a male subject, comprising the step of administering to the subject the selective androgen receptor modulator compound of any of formulas I–VI and/or its analog, derivative, isomer, metabolite, pharmaceutically acceptable salt, pharmaceutical product, hydrate, N-oxide, prodrug, polymorph, crystal or any combination thereof, in an amount effective to suppress sperm production in the subject, thereby effecting contraception in the subject.

In another embodiment, the present invention provides a method of hormone therapy comprising the step of contacting an androgen receptor of a subject with the selective androgen receptor modulator compound of any of formulas I–VI and/or its analog, derivative, isomer, metabolite, pharmaceutically acceptable salt, pharmaceutical product, hydrate, N-oxide, prodrug, polymorph, crystal or any combination thereof, in an amount effective to effect a change in an androgen-dependent condition.

In another embodiment, the present invention provides a method of hormone replacement therapy comprising the step of contacting an androgen receptor of a subject with the selective androgen receptor modulator compound of any of formulas I–VI and/or its analog, derivative, isomer, metabolite, pharmaceutically acceptable salt, pharmaceutical product, hydrate, N-oxide, prodrug, polymorph, crystal or any combination thereof, in an amount effective to effect a change in an androgen-dependent condition.

In another embodiment, the present invention provides a method of treating a subject having a hormone related condition, comprising the step of administering to the subject the selective androgen receptor modulator compound of any of formulas I–VI and/or its analog, derivative, isomer, metabolite, pharmaceutically acceptable salt, pharmaceutical product, hydrate, N-oxide, prodrug, polymorph, crystal or any combination thereof, in an amount effective to effect a change in an androgen-dependent condition.

In another embodiment, the present invention provides a method of treating a subject suffering from prostate cancer, comprising the step of administering to said subject the selective androgen receptor modulator compound of formulas I–VI and/or its analog, derivative, isomer, metabolite, pharmaceutically acceptable salt, pharmaceutical product, hydrate, N-oxide, prodrug, polymorph, crystal or any combination thereof, in an amount effective to treat prostate cancer in the subject.

In another embodiment, the present invention provides a method of preventing prostate cancer in a subject, comprising the step of administering to the subject the selective androgen receptor modulator compound of formulas I–VI and/or its analog, derivative, isomer, metabolite, pharmaceutically acceptable salt, pharmaceutical product, hydrate, N-oxide, prodrug, polymorph, crystal or any combination thereof, in an amount effective to prevent prostate cancer in the subject.

In another embodiment, the present invention provides a method of delaying the progression of prostate cancer in a subject suffering from prostate cancer, comprising the step of administering to said subject the selective androgen receptor modulator compound of formulas I–VI and/or its analog; derivative, isomer, metabolite, pharmaceutically acceptable salt, pharmaceutical product, hydrate, N-oxide, prodrug, polymorph, crystal or any combination thereof, in an amount effective to delay the progression of prostate cancer in the subject.

In another embodiment, the present invention provides a method of preventing the recurrence of prostate cancer in a subject suffering from prostate cancer, comprising the step of administering to said subject the selective androgen receptor modulator compound of formulas I–VI and/or its analog, derivative, isomer, metabolite, pharmaceutically acceptable salt, pharmaceutical product, hydrate, N-oxide, prodrug, polymorph, crystal or any combination thereof, in an amount effective to prevent the recurrence of prostate cancer in the subject.

In another embodiment, the present invention provides a method of treating the recurrence of prostate cancer in a subject suffering from prostate cancer, comprising the step of administering to said subject the selective androgen receptor modulator. compound of formulas I–VI and/or its analog, derivative, isomer, metabolite, pharmaceutically acceptable salt, pharmaceutical product, hydrate, N-oxide, prodrug, polymorph, crystal or any combination thereof, in an amount effective to treat the recurrence of prostate cancer in the subject.

In another embodiment, the present invention provides a method of treating a dry eye condition in a subject suffering from dry eyes, comprising the step of contacting an androgen receptor of a subject with the selective androgen receptor modulator compound of any of formulas I–VI and/or its analog, derivative, isomer, metabolite, pharmaceutically acceptable salt, pharmaceutical product, hydrate, N-oxide, prodrug, polymorph, crystal or any combination thereof, in an amount effective to treat dry eyes in the subject.

In another embodiment, the present invention provides a method of preventing a dry eye condition in a subject, comprising the step of contacting an androgen receptor of a subject with the selective androgen receptor modulator compound of any of formulas I–VI and/or its analog, derivative, isomer, metabolite, pharmaceutically acceptable salt, pharmaceutical product, hydrate, N-oxide, prodrug, polymorph, crystal or any combination thereof, in an amount effective to prevent dry eyes in the subject.

In another embodiment, the present invention provides a a method of inducing apoptosis in a cancer cell, comprising the step of contacting the cell with with the selective androgen receptor modulator compound of any of formulas I–VI and/or its analog, derivative, isomer, metabolite, pharmaceutically acceptable salt, pharmaceutical product, hydrate, N-oxide, prodrug, polymorph, crystal or any combination thereof, in an amount effective to induce apoptosis in the cancer cell.

The novel selective androgen receptor modulator compounds of the present invention, either alone or as a pharmaceutical composition, are useful for a) male contraception; b) treatment of a variety of hormone-related conditions, for example conditions associated with ADAM, such as fatigue, depression, decreased libido, sexual dysfunction, erectile dysfunction, hypogonadism, osteoporosis, hair loss, obesity, sarcopenia, osteopenia, benign prostate hyperplasia, and alterations in mood and cognition; c) treatment of conditions associated with ADIF, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of acute and/or chronic muscular wasting conditions; e) preventing and/or treating dry eye conditions; f) oral androgen replacement therapy; g) decreasing the incidence of, halting or causing a regression of prostate cancer; and/or h) inducing apoptosis in a cancer cell.

The selective androgen receptor modulator compounds of the present invention offer a significant advance over steroidal androgen treatment. Several of the selective androgen receptor modulator compounds of the present invention have unexpected androgenic and anabolic activity of a nonsteroidal ligand for the androgen receptor. Other selective androgen receptor modulator compounds of the present invention have unexpected antiandrogenic activity of a nonsteroidal ligand for the androgen receptor. Thus, treatment with the selective androgen receptor modulator compounds of the present invention will not be accompanied by serious side effects, inconvenient modes of administration, or high costs and will still have the advantages of oral bioavailability, lack of cross-reactivity with other steroid receptors, and long biological half-lives.

DETAILED DESCRIPTION OF THE INVENTION

This invention provides a class of androgen receptor targeting agents (ARTA). The agents define a new subclass of compounds, which are selective androgen receptor modulators (SARM). Several of the SARM compounds have been found to have an unexpected androgenic and anabolic activity of a nonsteroidal ligand for the androgen receptor. Other SARM compounds have been found to have an unexpected antiandrogenic activity of a nonsteroidal ligand for the androgen receptor. The SARM compounds, either alone or as a composition, are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of acute and/or chronic muscular wasting conditions; e) preventing and/or treating dry eye conditions; f) oral androgen replacement therapy; g) decreasing the incidence of, halting or causing a regression of prostate cancer; and/or h) inducing apoptosis in a cancer cell.

In one embodiment, the present invention provides a selective androgen receptor modulator (SARM) compound represented by the structure of formula I:

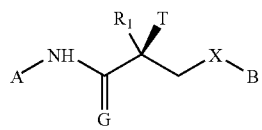

I wherein
X is a bond, O, $CH_2$, NH, Se, PR, NO or NR;
G is O or S;
$R_1$ is $CH_3$, $CH_2F$, $CHF_2$, $CF_3$, $CH_2CH_3$, or $CF_2CF_3$;
T is OH, OR, $NHCOCH_3$, or NHCOR;
R is alkyl, haloalkyl, dihaloalkyl, trihaloalkyl, $CH_2F$, $CHF_2$, $CF_3$, $CF_2CF_3$, aryl, phenyl, F, Cl, Br I, alkenyl or OH;
A is a ring selected from:

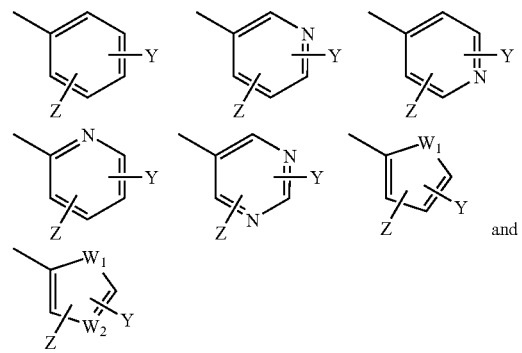

and

B is a ring selected from:

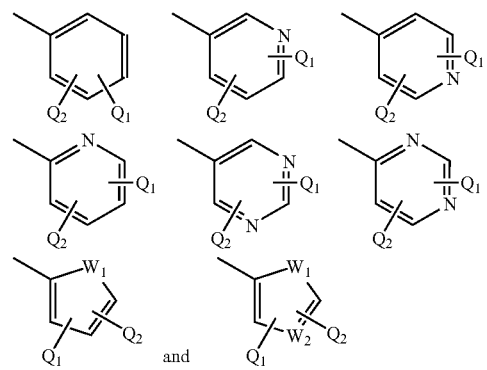

and wherein A and B cannot simultaneously be a benzene ring;
Z is $NO_2$, CN, COOH, COR, NHCOR or CONHR;
Y is $CF_3$, F, I, Br, Cl, CN, $C(R)_3$ or $Sn(R)_3$;
$Q_1$ and $Q_2$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR,

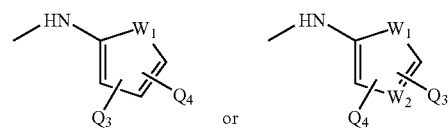

or $Q_3$ and $Q_4$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$ or SR;
$W_1$ is O, NH, NR, NO or S; and
$W_2$ is N or NO.

In one embodiment, this invention provides an analog of the compound of formula I. In another embodiment, this invention provides a derivative of the compound of formula I. In another embodiment, this invention provides an isomer of the compound of formula I. In another embodiment, this invention provides a metabolite of the compound of formula I. In another embodiment, this invention provides a pharmaceutically acceptable salt of the compound of formula I. In another embodiment, this invention provides a pharmaceutical product of the compound of formula I. In another embodiment, this invention provides a hydrate of the compound of formula I. In another embodiment, this invention provides an N-oxide of the compound of formula I. In another embodiment, this invention provides an impurity of the compound of formula I. In another embodiment, this invention provides a prodrug of the compound of formula I. In another embodiment, this invention provides a polymorph of the compound of formula I. In another embodiment, this invention provides a crystal of the compound of formula I. In another embodiment, this invention provides a combination of any of an analog, derivative, metabolite, isomer, pharmaceutically acceptable salt, pharmaceutical product, hydrate, N-oxide, impurity, prodrug, polymorph or crystal of the compound of formula I.

In one embodiment, the present invention provides a SARM compound of formula I wherein X is O. In another embodiment, the SARM compound is a compound of formula I wherein G is O; In another embodiment, the SARM compound is a compound of formula I wherein T is OH. In another embodiment, the SARM compound is a compound of formula I wherein $R_1$ is $CH_3$. In another embodiment, the SARM compound is a compound of formula I wherein Z is $NO_2$. In another embodiment, the, SARM compound is a compound of formula I wherein Z is CN. In another embodiment, the SARM compound is a compound of formula I wherein Y is $CF_3$. In another embodiment, the SARM compound is a compound of formula I wherein $Q_1$ is $NHCOCH_3$. In another embodiment, the SARM compound is a compound of formula I wherein $Q_1$ is F.

In another embodiment, the compound of formula I is represented by the structure of formula Ia:

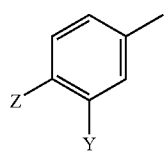

Ia wherein A and B are as defined above for compound I.

The substituents Z and Y can be in any position of the ring carrying these substituents (hereinafter "A ring"). In one embodiment, the substituent Z is in the para position of the A ring. In another embodiment, the substituent Y is in the meta position of the A ring. In another embodiment, the substituent Z is in the para position of the A ring and substituent Y is in the meta position of the A ring.

In one embodiment, the A ring is represented by the structure:

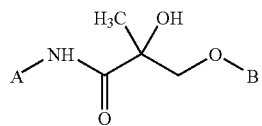

In another embodiment, the A ring is represented by the structure:

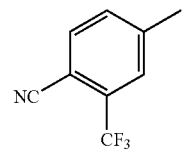

In another embodiment, the A ring is represented by the structure:

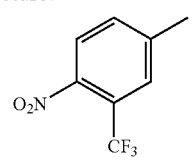

In another embodiment, the A ring is represented by the structure:

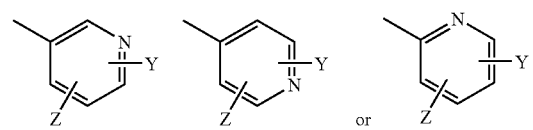

The substituents $Q_1$ and $Q_2$ can be in any position of the ring carrying these substituents (hereinafter "B ring"). In one embodiment, the substituent $Q_1$ is in the para position of the B ring. In another embodiment, the subsituent is $Q_2$ is H. In another embodiment, the substitutent $Q_1$ is in the para position of the B ring and the subsituent is $Q_2$ is H. In another embodiment, the substitutent $Q_1$ is $NHCOCH_3$ and is in the para position of the B ring, and the subsituent is $Q_2$ is H.

In one embodiment, the B ring is represented by the structure:

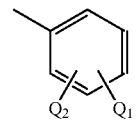

In another embodiment, the B ring is represented by the structure:

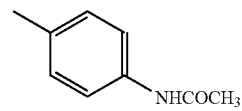

In another embodiment, the B ring is represented by the structure:

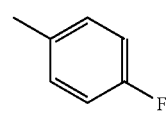

In another embodiment, the B ring is represented by the structure:

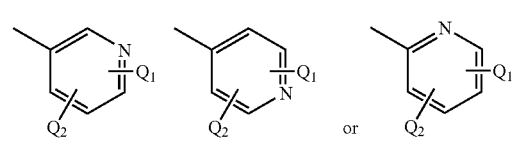

In one embodiment, the A ring is represented by either of the heterocyclic rings:

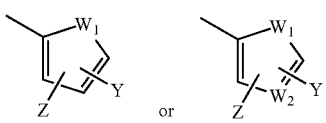

In another embodiment, the B ring is represented by either of the heterocyclic rings:

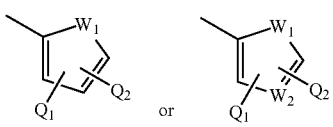

In one embodiment, the substituents $Q_1$ and/or $Q_2$ on the B ring are represented by either of the heterocyclic rings:

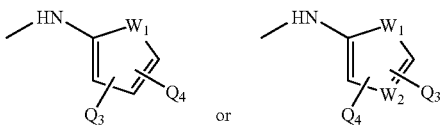

In these five-membered heterocyclic rings, $W_1$ is O, NH, NR, NO or S; and $W_2$ is N or NO. These heterocyclic rings cover a wide variety of heterocyclic rings, nonlimiting examples of which are pyrrole, imidazole, furan, thiophene, thiazole, oxazole, and the like. Furthermore, the heterocyclic rings wherein one of the ring members $W_1$ and/or $W_2$ represents nitrogen may be in the form of their corresponding N-oxides (NO).

The following examples illustrate certain nonlimiting embodiments of the SARM compounds that fall within the scope of the present invention. In one embodiment, the SARM compound is represented by the structure of formula II:

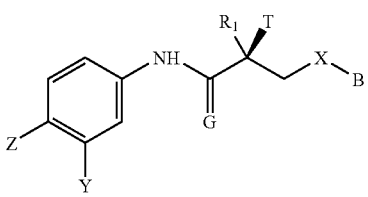

wherein

X is a bond, O, $CH_2$, NH, Se, PR, NO or NR;

G is O or S;

$R_1$ is $CH_3$, $CH_2F$, $CHF_2$, $CF_3$, $CH_2CH_3$, or $CF_2CF_3$;

T is OH, OR, $NHCOCH_3$, or NHCOR;

R is alkyl, haloalkyl, dihaloalkyl, trihaloalkyl, $CH_2F$, $CHF_2$, $CF_3$, $CF_2CF_3$; aryl, phenyl, F, Cl, Br, I, alkenyl or OH;

B is a ring selected from:

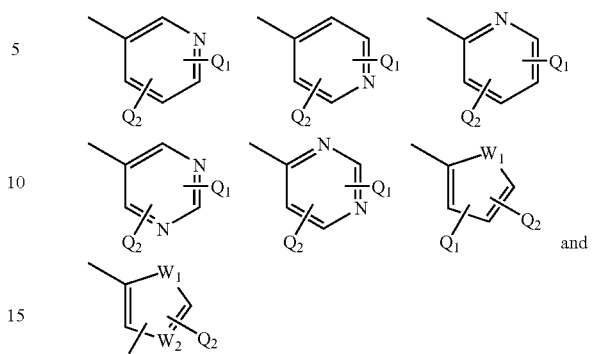

Z is $NO_2$, CN, COOH, COR, NHCOR or CONHR;

Y is $CF_3$, F, I, Br, Cl, CN, $C(R)_3$ or $Sn(R)_3$;

$Q_1$ and $Q_2$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR,

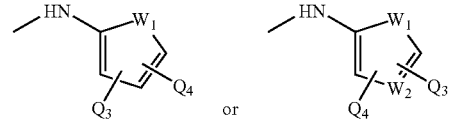

$Q_3$ and $Q_4$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$ or SR;

$W_1$ is O, NH, NR, NO or S; and $W_2$ is N or NO.

In one embodiment, this invention provides an analog of the compound of formula II. In another embodiment, this invention provides a derivative of the compound of formula II. In another embodiment, this invention provides an isomer of the compound of formula II. In another embodiment, this invention provides a metabolite of the compound of formula II. In another embodiment, this invention provides a pharmaceutically acceptable salt of the compound of formula II. In another embodiment, this invention provides a pharmaceutical product of the compound of formula II. In another embodiment, this invention provides a hydrate of the compound of formula II. In another embodiment, this invention provides an N-oxide of the compound of formula II. In another embodiment, this invention provides an impurity of the compound of formula II. In another embodiment, this invention provides a prodrug of the compound of formula II. In another embodiment, this invention provides a polymorph of the compound of formula II. In another embodiment, this invention provides a crystal of the compound of formula II In another embodiment, this invention provides a combination of any of an analog, derivative, metabolite, isomer, pharmaceutically acceptable salt, pharmaceutical product, hydrate, N-oxide, impurity, prodrug, polymorph or crystal of the compound of formula II.

In one embodiment, the present invention provides a SARM compound of formula II wherein X is O. In another embodiment, the SARM compound is a compound of formula II wherein G is O. In another embodiment, the SARM compound is a compound of formula II wherein T is OH. In another embodiment, the SARM compound is a compound of formula II wherein $R_1$ is $CH_3$. In another embodiment, the SARM compound is a compound of formula II wherein Z is $NO_2$. In another embodiment, the SARM compound is a compound of formula II wherein Z is CN. In another embodiment, the SARM compound is a compound of formula II wherein Y is $CF_3$. In another embodiment, the SARM compound is a compound of formula II wherein $Q_1$ is $NHCOCH_3$. In another embodiment, the SARM compound is a compound of formula II wherein $Q_1$ is F.

In one embodiment, the selective androgen receptor modulator compound is represented by the structure of formula III, wherein B and X are as defined above for the SARM compound of formula II.

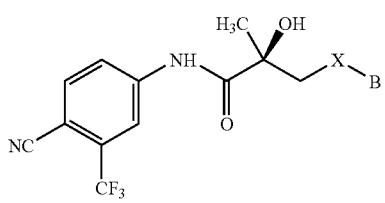

III

In one embodiment, this invention provides an analog of the compound of formula III. In another embodiment, this invention provides a derivative of the compound of formula III. In another embodiment, this invention provides an isomer of the compound of formula III. In another embodiment, this invention provides a metabolite of the compound of formula III. In another embodiment, this invention provides a pharmaceutically acceptable salt of the compound of formula III. In another embodiment, this invention provides a pharmaceutical product of the compound of formula III. In another embodiment, this invention provides a hydrate of the compound of formula III. In another embodiment, this invention provides a n N-oxide of the compound of formula III. In another embodiment, this invention provides an impurity of the compound of formula III. In another embodiment, this invention provides a prodrug of the compound of formula III. In another embodiment, this invention provides a polymorph of the compound of formula III. In another embodiment, this invention provides a crystal of the compound of formula III. In another embodiment, this invention provides a combination of any of an analog, derivative, metabolite, isomer, pharmaceutically acceptable salt, pharmaceutical product, hydrate, N-oxide, impurity, prodrug, polymorph or crystal of the compound of formula III.

In another embodiment, the selective androgen receptor modulator compound is represented by the structure of formula IV, wherein B and X are as defined above for the SARM compound of formula II.

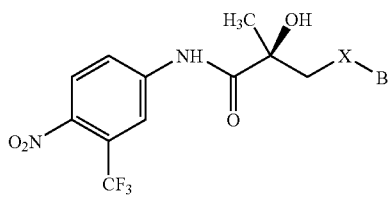

IV

In one embodiment, this invention provides an analog of the compound of formula IV. In another embodiment, this invention provides a derivative of the compound of formula IV. In another embodiment, this invention provides an isomer of the compound of formula IV. In another embodiment, this invention provides a metabolite of the compound of formula IV. In another embodiment, this invention provides a pharmaceutically acceptable salt of the compound of formula IV. In another embodiment, this invention provides a pharmaceutical product of the compound of formula IV. In another embodiment, this invention provides a hydrate of the compound of formula IV. In another embodiment, this invention provides a n N-oxide of the compound of formula IV. In another embodiment, this invention provides an impurity of the compound of formula IV. In another embodiment, this invention provides a prodrug of the compound of formula IV. In another embodiment, this invention provides a polymorph of the compound of formula IV. In another embodiment, this invention provides a crystal of the compound of formula IV. In another embodiment, this invention provides a combination of any of an analog, derivative, metabolite, isomer, pharmaceutically acceptable salt, pharmaceutical product, hydrate, N-oxide, impurity, prodrug, polymorph or crystal of the compound of formula IV.

In another embodiment, the selective androgen receptor modulator compound is represented by the structure:

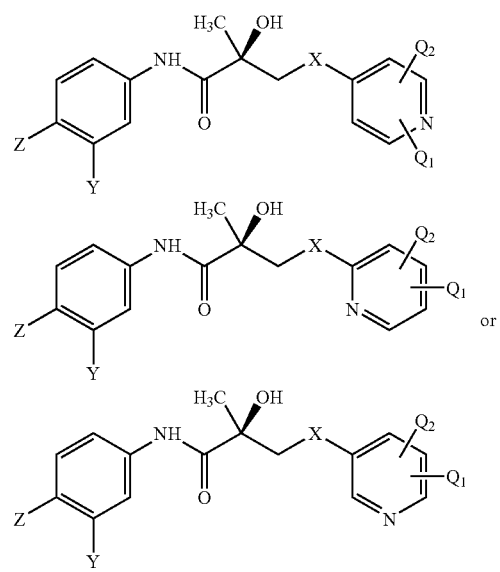

or

In another embodiment, the selective androgen receptor modulator compound is represented by the structure:

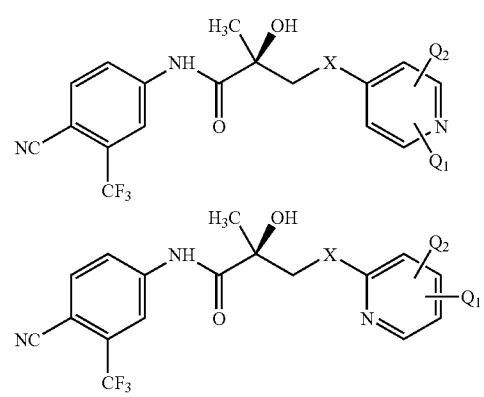

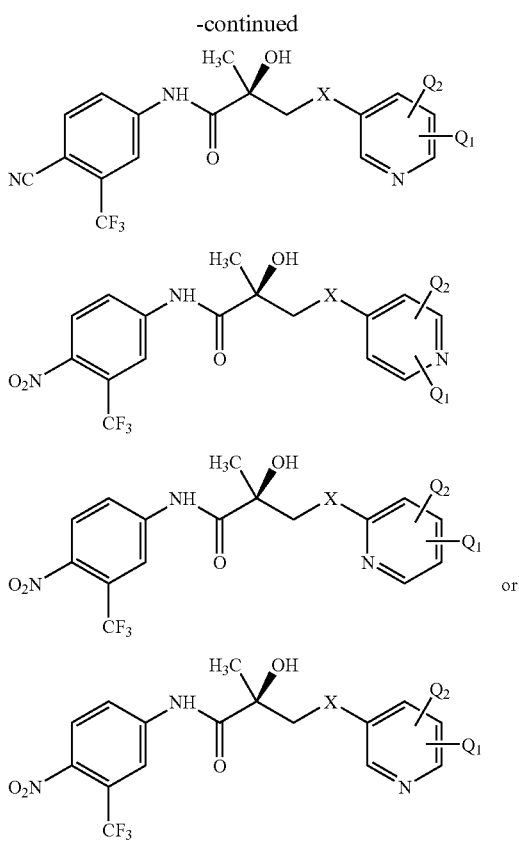

In another embodiment, the selective androgen receptor modulator compound is represented by the structure

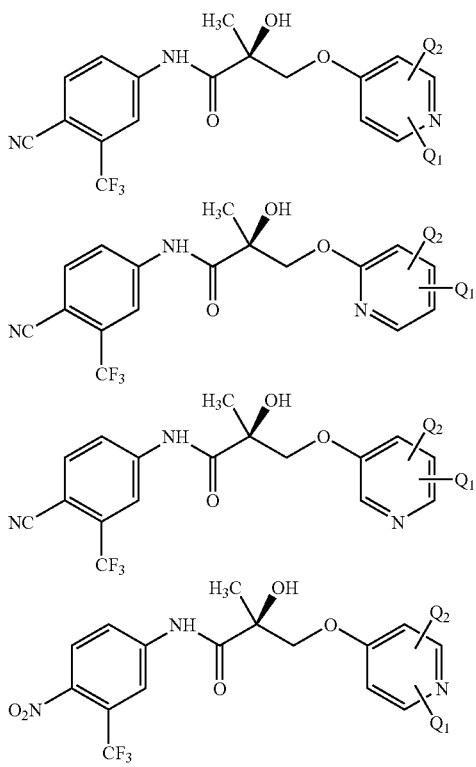

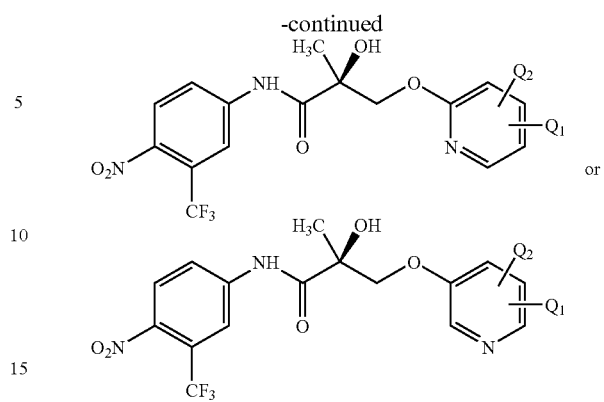

In another embodiment, the selective androgen receptor modulator compound of the present invention is represented by the structure of formula V:

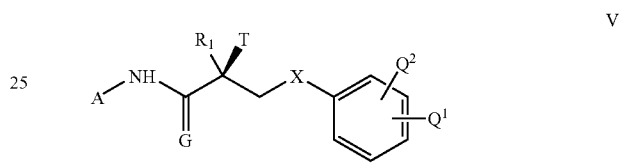

wherein
X is a bond, O, CH$_2$, NH, Se, PR, NO or NR;
G is O or S;
R$_1$ is CH$_3$, CH$_2$F, CHF$_2$, CF$_3$, CH$_2$CH$_3$, or CF$_2$CF$_3$;
T is OH, OR, NHCOCH$_3$, or NHCOR;
R is alkyl, haloalkyl, dihaloalkyl, trihaloalkyl, CH$_2$F, CHF$_2$, CF$_3$, CF$_2$CF$_3$; aryl, phenyl, F, Cl, Br, I, alkenyl or OH;
A is a ring selected from:

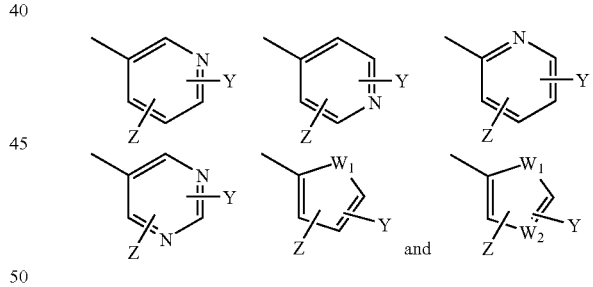

Z is NO$_2$, CN, COOH, COR, NHCOR or CONHR;
Y is CF$_3$, F, I, Br, Cl, CN, C(R)$_3$ or Sn(R)$_3$;
Q$_1$ and Q$_2$ are independently of each other a hydrogen, alkyl, F, Cl, Br, I, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR NHCSCH$_3$, NHCSCF$_3$, NHCSR, NHSO$_2$CH$_3$, NHSO$_2$R, OR, COR, OCOR, OSO$_2$R, SO$_2$R, SR,

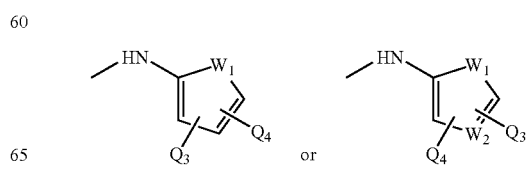

Q₃ and Q₄ are independently of each other a hydrogen, alkyl, F, Cl, Br, I, CF₃, CN, C(R)₃, Sn(R)₃, N(R)₂, NHCOCH₃, NHCOCF₃, NHCOR, NHCONHR, NHCOOR, OCONHR, CONHR, NHCSCH₃, NHCSCF₃, NHCSR NHSO₂CH₃, NHSO₂R, OR, COR, OCOR, OSO₂R, SO₂R or SR;

W₁ is O, NH, NR, NO or S; and

W₂ is N or NO.

In one embodiment, this invention provides an analog of the compound of formula V. In another embodiment, this invention provides a derivative of the compound of formula V. In another embodiment, this invention provides an isomer of the compound of formula V. In another embodiment, this invention provides a metabolite of the compound of formula V. In another embodiment, this invention provides a pharmaceutically acceptable salt of the compound of formula V. In another embodiment, this invention provides a pharmaceutical product of the compound of formula V. In another embodiment, this invention provides a hydrate of the compound of formula V. In another embodiment, this invention provides an N-oxide of the compound of formula V. In another embodiment, this invention provides an impurity of the compound of formula V. In another embodiment, this invention provides a prodrug of the compound of formula V. In another embodiment, this invention provides a polymorph of the compound of formula V. In another embodiment, this invention provides a crystal of the compound of formula V. In another embodiment, this invention provides a combination of any of an analog, derivative, metabolite, isomer, pharmaceutically acceptable salt, pharmaceutical product, hydrate, N-oxide, impurity, prodrug, polymorph or crystal of the compound of formula V.

In one embodiment, the present invention provides a SARM compound of formula V wherein X is O. In another embodiment, the SARM compound is a compound of formula II wherein G is O. In another embodiment, the SARM compound is a compound of formula V wherein T is OH. In another embodiment, the SARM compound is a compound of formula V wherein R₁ is CH₃. In another embodiment, the SARM compound is a compound of formula V wherein Z is NO₂. In another embodiment, the SARM compound is a compound of formula V wherein Z is CN. In another embodiment, the SARM compound is a compound of formula V wherein Y is CF₃. In another embodiment, the SARM compound is a compound of formula V wherein Q₁ is NHCOCH₃. In another embodiment, the SARM compound is a compound of formula V wherein Q₁ is F.

In another embodiment, the selective androgen receptor modulator compound of the present invention is represented by the structure of formula VI, wherein A and X are as defined above for formula V.

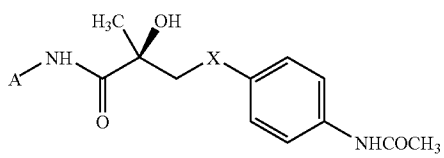

VI

In one embodiment, this invention provides an analog of the compound of formula VI. In another embodiment, this invention provides a derivative of the compound of formula VI. In another embodiment, this invention provides an isomer of the compound of formula VI. In another embodiment, this invention provides a metabolite of the compound of formula VI. In another embodiment, this invention provides a pharmaceutically acceptable salt of the compound of formula VI. In another embodiment, this invention provides a pharmaceutical product of the compound of formula VI. In another embodiment, this invention provides a hydrate of the compound of formula VI. In another embodiment, this invention provides an N-oxide of the compound of formula VI. In another embodiment, this invention provides an impurity of the compound of formula VI. In another embodiment, this invention provides a prodrug of the compound of formula VI. In another embodiment, this invention provides a polymorph of the compound of formula VI. In another embodiment, this invention provides a crystal of the compound of formula VI. In another embodiment, this invention provides a combination of any of an analog, derivative, metabolite, isomer, pharmaceutically acceptable salt, pharmaceutical product, hydrate, N-oxide, impurity, prodrug, polymorph or crystal of the compound of formula VI.

In another embodiment, the selective androgen receptor modulator compound is represented by the structure:

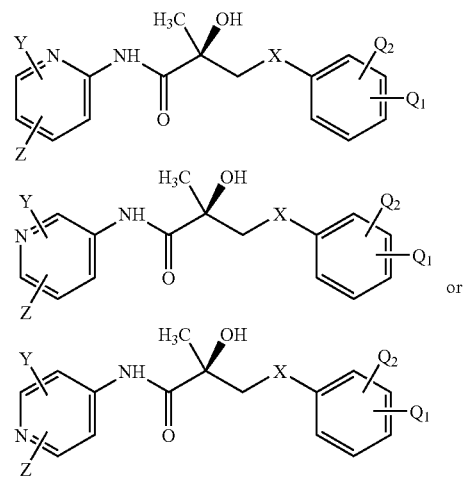

or

In another embodiment, the selective androgen receptor modulator compound is represented by the structure:

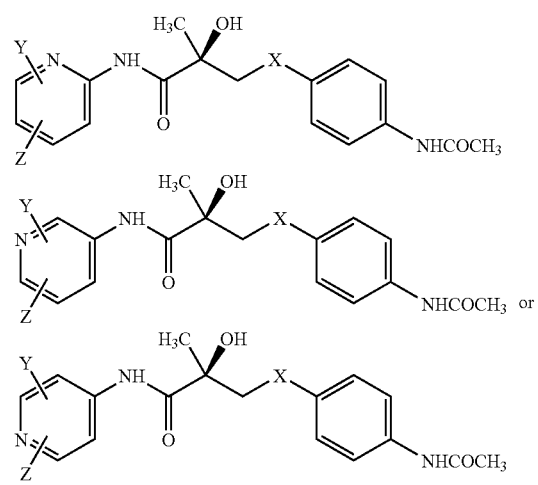

In another embodiment, the selective androgen receptor modulator compound is represented by the structure:

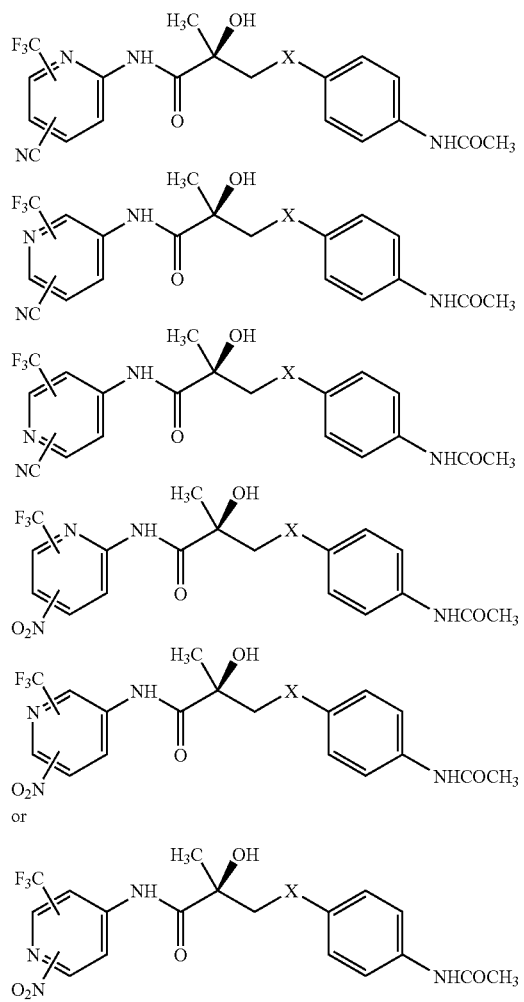

In another embodiment, the selective androgen receptor modulator compound is represented by the structure:

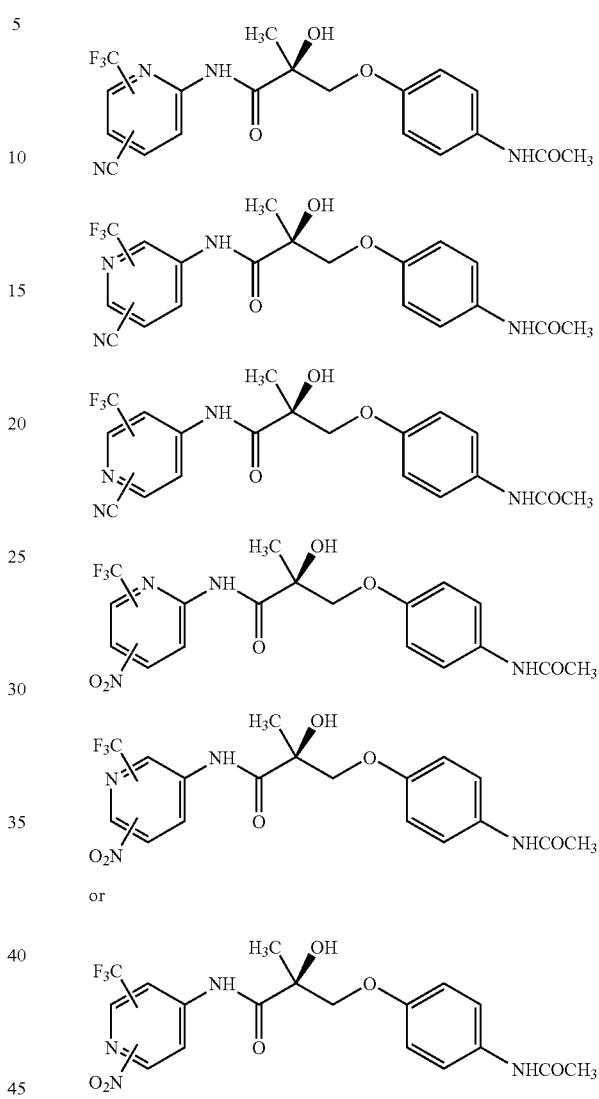

In another embodiment, the selective androgen receptor modulator compound is represented by the structure:

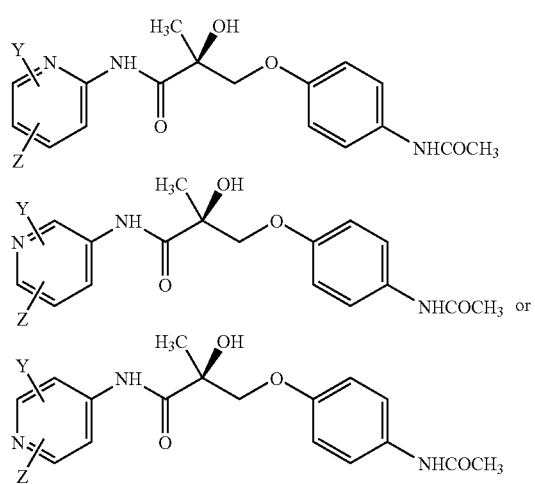

In another embodiment, the selective androgen receptor modulator compound is represented by the structure:

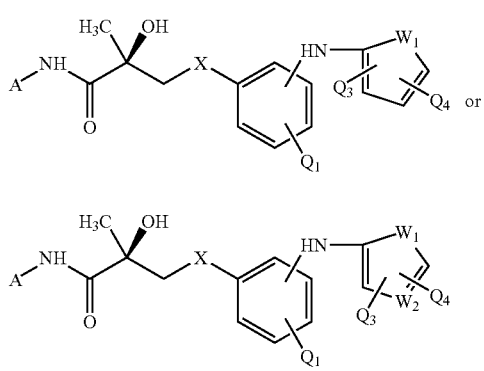

In another embodiment, the selective androgen receptor modulator compound is represented by the structure:

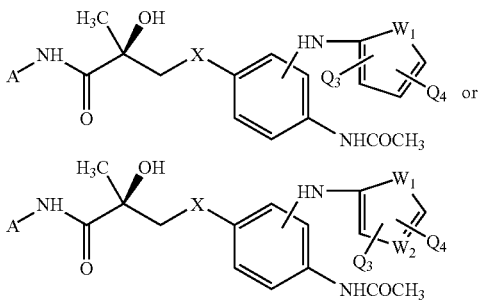

In another embodiment, the selective androgen receptor modulator compound is represented by the structure:

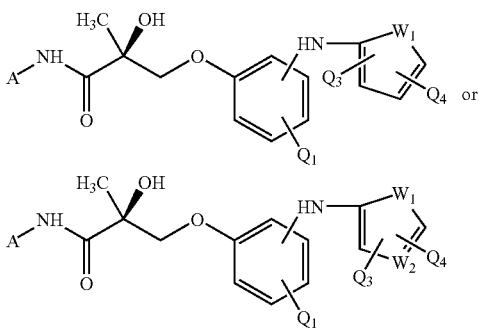

In another embodiment, the selective. androgen receptor modulator compound is represented by the structure:

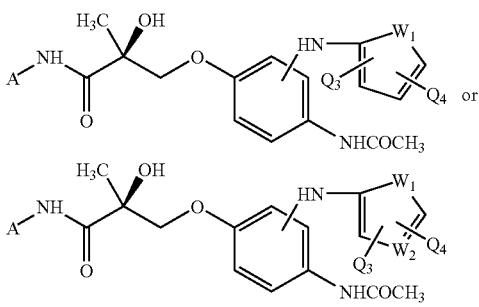

Definitions

The substituent R is defined herein as an alkyl, haloalkyl, dihaloalkyl, trihaloalkyl, $CH_2F$, $CHF_2$, $CF_3$, $CF_2CF_3$; aryl, phenyl, F, Cl, Br, I, alkenyl, or hydroxyl (OH).

An "alkyl" group refers to a saturated aliphatic hydrocarbon, including straight-chain, branched-chain and cyclic alkyl groups. In one embodiment, the alkyl group has 1–12 carbons. In another embodiment, the alkyl group has 1–7 carbons. In another embodiment, the alkyl group has 1–6 carbons. In another embodiment, the alkyl group has 1–4 carbons. The alkyl group may be unsubstituted or substituted by one or more groups selected from halogen (e.g. F, Cl, Br, I), hydroxy, alkoxy carbonyl, amido, alkylamido, dialkylamido, nitro, amino, alkylamino, dialkylamino, carboxyl, thio and thioalkyl.

A "haloalkyl" group refers to an alkyl group as defined above, which is substituted by one or more halogen atoms, e.g. by F, Cl, Br or I. A "halogen" refers to elements of Group VII or the periodic table, e.g. F, Cl, Br or I.

An "aryl" group refers to an aromatic group having at least one carbocyclic aromatic group or heterocyclic aromatic group, which may be unsubstituted or substituted by one or more groups selected from halogen (e.g. F, Cl, Br, I), haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers to an OH group. An "alkenyl" group refers to a group having at least one carbon to carbon double bond.

An "arylalkyl" group refers to an alkyl bound to an aryl, wherein alkyl and aryl are as defined above. An example of an aralkyl group is a benzyl group.

As contemplated herein, the present invention relates to the use of a SARM compound and/or its analog, derivative, isomer, metabolite, pharmaceutically acceptable salt, pharmaceutical product, hydrate, N-oxide, prodrug, polymorph or crystal or combinations thereof. In one embodiment, the invention relates to the use of an analog of the SARM compound. In another embodiment, the invention relates to the use of a derivative of the SARM compound. In another embodiment, the invention relates to the use of an isomer of the SARM compound. In another embodiment, the invention relates to the use of a metabolite of the SARM compound. In another embodiment, the invention relates to the use of a pharmaceutically acceptable salt of the SARM compound. In another embodiment, the invention relates to the use of a pharmaceutical product of the SARM compound. In another embodiment, the invention relates to the use of a hydrate of the SARM compound. In another embodiment, the invention relates to the use of an N-oxide of the SARM compound. In another embodiment, the invention relates to the use of a prodrug of the SARM compound. In another embodiment, the invention relates to the use of a polymorph of the SARM compound. In another embodiment, the invention relates to the use of a crystal of the SARM compound. In another embodiment, the invention relates to the use of any of a combination of an analog, derivative, isomer, metabolite, pharmaceutically acceptable salt, pharmaceutical product, hydrate, or N-oxide, prodrug, polymorph or crystal of the SARM compounds of the present invention.

As defined herein, the term "isomer" includes, but is not limited to, optical isomers and analogs, structural isomers and analogs, conformational isomers and analogs, and the like.

In one embodiment, this invention encompasses the use of various optical isomers of the SARM compounds. It will be appreciated by those skilled in the art that the SARM compounds of the present invention contain at least one chiral center. Accordingly, the SARM compounds used in the methods of the present invention may exist in, and be isolated in, optically-active or racemic forms. Some compounds may also exhibit polymorphism. It is to be understood that the present invention encompasses any racemic, optically-active, polymorphic, or stereroisomeric form, or mixtures thereof, which form possesses properties useful in the methods as described herein. In one embodiment, the SARM compounds are the pure (R)-isomers. In another embodiment, the SARM compounds are the pure (S)-isomers. In another embodiment, the SARM compounds are a mixture of the (R) and the (S) isomers. In another embodiment, the SARM compounds are a racemic mixture comprising an equal amount of the (R) and the, (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

This invention further includes derivatives of the SARM compounds. The term "derivatives" includes but is not limited to ether derivatives, acid derivatives, amide derivatives, ester derivatives and the like. In addition, this invention further includes hydrates of the SARM compounds. The term "hydrate" includes but is not limited to hemihydrate, monohydrate, dihydrate, trihydrate and the like.

This invention further includes metabolites of the SARM compounds. The term "metabolite" means any substance produced from another substance by metabolism or a metabolic process.

This invention further includes pharmaceutical products of the SARM compounds. The term "pharmaceutical product" means a composition suitable for pharmaceutical use (pharmaceutical composition), as defined herein.

This invention further includes prodrugs of the SARM compounds. The term "prodrug" means a substance which can be converted in-vivo into a biologically active agent by such reactions as hydrolysis, esterification, desterification, activation, salt formation and the like.

This invention further includes crystals of the SARM compounds. Furthermore, this invention provides polymorphs of the SARM compounds. The term "crystal" means a substance in a crystalline state. The term "polymorph" refers to a particular crystalline state of a substance, having particular physical properties such as X-ray diffraction, IR spectra, melting point, and the like.

Biological Activity of Selective Androgen Receptor Modulator Compounds

Selective androgen receptor modulator (SARM) compounds are a novel class of androgen receptor targeting agents ("ARTA"), that have previously been shown to be useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of acute and/or chronic muscular wasting conditions; e) preventing and/or treating dry eye conditions; f) oral androgen replacement therapy; g) decreasing the incidence of, halting or causing a regression of prostate cancer; and/or h) inducing apoptosis in a cancer cell.

As used herein, receptors for extracellular signaling molecules are collectively referred to as "cell signaling receptors". Many cell signaling receptors are transmembrane proteins on a cell surface; when they bind an extracellular signaling molecule (i.e., a ligand), they become activated so as to generate a cascade of intracellular signals that alter the behavior of the cell. In contrast, in some cases, the receptors are inside the cell and the signaling ligand has to enter the cell to activate them; these signaling molecules therefore must be sufficiently small and hydrophobic to diffuse across the plasma membrane of the cell.

Steroid hormones are one example of small hydrophobic molecules that diffuse directly across the plasma membrane of target cells and bind to intracellular cell signaling receptors. These receptors are structurally related and constitute the intracellular receptor superfamily (or steroid-hormone receptor superfamily). Steroid hormone receptors include progesterone receptors, estrogen receptors, androgen receptors, glueocorticoid receptors, and mineralocorticoid receptors. The present invention is particularly directed to androgen receptors.

In addition to ligand binding to the receptors, the receptors can be blocked to prevent ligand binding. When a substance binds to a receptor, the three-dimensional structure of the substance fits into a space created by the three-dimensional structure of the receptor in a ball and socket configuration. The better the ball fits into the socket, the more tightly it is held. This phenomenon is called affinity. If the affinity of a substance is greater than the original hormone, it will compete with the hormone and bind the binding site more frequently. Once bound, signals may be sent through the receptor into the cell, causing the cell to respond in some fashion. This is called activation. On activation, the activated receptor then directly regulates the transcription of specific genes. But the substance and the receptor may have certain attributes, other than affinity, in order to activate the cell. Chemical bonds between atoms of the substance and the atoms of the receptors may form. In some cases, this leads to a change in the configuration of the receptor, which is enough to begin the activation process (called signal transduction).

In one embodiment, the present invention is directed to selective androgen receptor modulator compounds which are agonist compounds. A receptor agonist is a substance which binds receptors and activates them. Thus, in one embodiment, the SARM compounds of the present invention are useful in binding to and activating steroidal hormone receptors. In one embodiment, the agonist compound of the present invention is an agonist which binds the androgen receptor. In another embodiment, the compound has high affinity for the androgen receptor. In another embodiment, the agonist compound also has anabolic activity. In another embodiment, the present invention provides selective androgen modulator compounds which have agonistic and anabolic activity of a nonsteroidal compound for the androgen receptor.

In another embodiment, the present invention is directed to selective androgen receptor modulator compounds which are antagonist compounds. A receptor antagonist is a substance which binds receptors and inactivates them. Thus, in one embodiment, the SARM compounds of the present invention are useful in binding to and inactivating steroidal hormone receptors. In one embodiment, the antagonist compound of the present invention is an antagonist which binds the androgen receptor. In another embodiment, the compound has high affinity for the androgen receptor.

In yet another embodiment, the SARM compounds of the present invention can be classified as partial AR agonist/antagonists. The SARMs are AR agonists in some tissues, to cause increased transcription of AR-responsive genes (e.g. muscle anabolic effect). In other tissues, these compounds serve as inhibitors at the AR to prevent agonistic effects of the native androgens.

Assays to determine whether the compounds of the present invention are AR agonists or antagonists are well known to a person skilled in the art. For example, AR agonistic activity can be determined by monitoring the ability of the SARM compounds to maintain and/or stimulate the growth of AR containing tissue such as prostate and seminal vesicles, as measured by weight. AR antagonistic activity can be determined by monitoring the ability of the SARM compounds to inhibit the growth of AR containing tissue.

The compounds of the present invention bind either reversibly or irreversibly to an androgen receptor. In one embodiment, the androgen receptor is an androgen receptor of a mammal. In another embodiment, the androgen receptor is an androgen receptor of a human. In one embodiment, the SARM compounds bind reversibly to the androgen receptor of a mammal, for example a human. Reversible binding of a compound to a receptor means that a compound can detach from the receptor after binding.

In another embodiment, the SARM compounds bind irreversibly to the androgen receptor of a mammal, for example a human. Thus, in one embodiment, the compounds of the present invention may contain a functional group (e.g. affinity label) that allows alkylation of the androgen receptor (i.e. covalent bond formation). Thus, in this case, the compounds are alkylating agents which bind irreversibly to the receptor and, accordingly, cannot be displaced by a steroid, such as the endogenous ligands DHT and testosterone. An "alkylating agent" is defined herein as an agent which alkylates (forms a covalent bond) with a cellular component, such as DNA, RNA or enzyme. It is a highly reactive chemical that introduces alkyl radicals into biologically active molecules and thereby prevents their proper functioning. The alkylating moiety is an electrophilic group that interacts with nucleophilic moieties in cellular components.

According to one embodiment of the present invention, a method is provided for binding the SARM compounds of the present invention to an androgen receptor by contacting the receptor with a SARM compound and/or its analog, derivative, isomer, metabolite, pharmaceutically acceptable salt, pharmaceutical product, hydrate, N-oxide, prodrug, polymorph, crystal or any combination thereof, under conditions effective to cause the selective androgen receptor modulator compound to bind the androgen receptor. The binding of the selective androgen receptor modulator compounds to the androgen receptor enables the compounds of the present invention to be useful as a male contraceptive and in a number of hormone therapies. The agonist compounds bind to and activate the androgen-receptor. The antagonist compounds bind to and inactivate the androgen receptor. Binding of the agonist or antagonist compounds is either reversible or irreversible.

According to one embodiment of the present invention, a method is provided for suppressing spermatogenesis in a subject by contacting an androgen receptor of the subject with a SARM compound of the present invention and/or its analog, derivative, isomer, metabolite, pharmaceutically acceptable salt, pharmaceutical product, hydrate, N-oxide, prodrug, polymorph, crystal or any combination thereof, in an amount effective to bind the selective androgen receptor modulator compound to the androgen receptor and suppress spermatogenesis.

In another embodiment, the present invention provides a method of contraception in a male subject, comprising the step of administering to the subject a SARM compound of the present invention, and/or its analog, derivative, isomer, metabolite, pharmaceutically acceptable salt, pharmaceutical product, hydrate, N-oxide, prodrug, polymorph, crystal or any combination thereof, in an amount effective to suppress sperm production in the subject, thereby effecting contraception in the subject.

According to another embodiment of the present invention, a method is provided for hormonal therapy in a patient (i.e., one suffering from an androgen-dependent condition) which includes contacting an androgen receptor of a patient with a SARM compound of the present invention and/or its analog, derivative, isomer, metabolite, pharmaceutically acceptable salt, pharmaceutical product, hydrate, N-oxide, prodrug, polymorph, crystal or any combination thereof, in an amount effective to bind the selective androgen receptor modulator compound to the androgen receptor and effect a change in an androgen-dependent condition.

According to another embodiment of the present invention, a method is provided for hormonal replacement therapy in a patient which includes contacting an androgen receptor of a patient with a SARM compound of the present invention and/or its analog, derivative, isomer, metabolite, pharmaceutically acceptable salt, pharmaceutical product, hydrate, N-oxide, prodrug, polymorph, crystal or any combination thereof, in an amount effective to bind the selective androgen receptor modulator compound to the androgen receptor and effect a change in an androgen-dependent condition.

According to another embodiment of the present invention, a method is provided for treating a subject having a hormone related condition which includes administering to the subject a SARM compound of the present invention and/or its analog, derivative, isomer, metabolite, pharmaceutically acceptable salt, pharmaceutical product, hydrate, N-oxide, prodrug, polymorph, crystal or any combination thereof, in an amount effective to bind the SARM compound to the androgen receptor and effect a change in an androgen-dependent condition.

Androgen-dependent conditions which may be treated according to the present invention include those conditions which are associated with aging, such as hypogonadism, sarcopenia, erythropoiesis, osteoporosis, and any other conditions. determined to be dependent upon low androgen (e.g., testosterone) levels.

According to another embodiment of the present invention, a method is provided for treating a subject suffering from prostate cancer, comprising the step of administering to the subject a SARM compound of the present invention and/or its analog, derivative, isomer, metabolite, pharmaceutically acceptable salt, pharmaceutical product, hydrate, N-oxide, prodrug, polymorph, crystal or any combination thereof, in an amount effective to treat prostate cancer in the subject.

According to another embodiment of the present invention, a method is provided for preventing prostate cancer in a subject, comprising the step of administering to the subject a SARM compound of the present invention and/or its analog, derivative, isomer, metabolite, pharmaceutically acceptable salt, pharmaceutical product, hydrate, N-oxide, prodrug, polymorph, crystal or any combination thereof, in an amount effective to prevent prostate cancer in the subject.

According to another embodiment of the present invention, a method is provided for delaying the progression of prostate cancer in a subject suffering from prostate cancer, comprising the step of administering to the subject a SARM compound of the present invention and/or its analog, derivative, isomer, metabolite, pharmaceutically acceptable salt, pharmaceutical product, hydrate, N-oxide, prodrug, polymorph, crystal or any combination thereof, in an amount effective to delay the progression of prostate cancer in the subject.

According to another embodiment of the present invention, a method is provided for preventing the recurrence of prostate cancer in a subject suffering from prostate cancer, comprising the step of administering to the subject a SARM compound of the present invention and/or its analog, derivative, isomer, metabolite, pharmaceutically acceptable salt, pharmaceutical product, hydrate, N-oxide, prodrug; polymorph, crystal or any combination thereof, in an amount effective to prevent the recurrence of prostate cancer in the subject.

According to another embodiment of the present invention, a method is provided for treating the recurrence of prostate cancer in a subject suffering from prostate cancer, comprising the step of administering to the subject a SARM compound of the present invention and/or its analog, derivative, isomer, metabolite, pharmaceutically acceptable salt, pharmaceutical product, hydrate, N-oxide, prodrug, polymorph, crystal or any combination thereof, in an amount effective to treat the recurrence of prostate cancer in the subject.

Furthermore, stimulation of the Androgen Receptor stimulates the production of tears, and thus the SARM compounds of the present invention may be used to treat dry eye conditions. Therefore, according to another embodiment of the present invention, a method is provided for treating a dry eye condition in a subject suffering from dry eyes, comprising the step of administering to said subject the selective androgen receptor modulator compound of the present invention and/or its analog, derivative, isomer, metabolite, pharmaceutically acceptable salt, pharmaceutical product, hydrate, N-oxide, prodrug, polymorph, crystal or any combination thereof, in an amount effective to treat dry eyes in the subject.

According to another embodiment of the present invention, a method is provided for preventing a dry eye condition in a subject, comprising the step of administering to said subject the selective androgen receptor modulator compound of the present invention and/or its analog, derivative, isomer, metabolite, pharmaceutically acceptable salt, pharmaceutical product, hydrate, N-oxide, prodrug, polymorph, crystal or any combination thereof, in an amount effective to prevent dry eyes in the subject.

In another embodiment, the present invention provides a a method of inducing apoptosis in a cancer cell, comprising the step of contacting the cell with with the selective androgen receptor modulator compound of the present invention and/or its analog, derivative, isomer, metabolite, pharmaceutically acceptable salt, pharmaceutical product, hydrate, N-oxide, prodrug, polymorph, crystal or any combination thereof, in an amount effective to induce apoptosis in said cancer cell.

As defined herein, "contacting" means that the SARM compound of the present invention is introduced into a sample containing the enzyme in a test tube, flask, tissue cultureor CHip, array, plate, microplate, capillary, or the like, and incubated at a temperature and time sufficient to permit binding of the SARM to the enzyme. Methods for contacting the samples with the SARM or other specific binding components are known to those skilled in the art and may be selected depending on the type of assay protocol to be run. Incubation methods are also standard and are known to those skilled in the art.

In another embodiment, the term "contacting" means that the SARM compound of the present invention is introduced into a subject receiving treatment, and the SARM compound is allowed to come in contact with the androgen receptor in vivo.

The term "libido, as used herein, means sexual desire.

The term "erectile", as used herein, means capable of being erected. An erectile tissue is a tissue, which is capable of being greatly dilated and made rigid by the distension of the numerous blood vessels which it contains.

"Hypogonadism" is a condition resulting from or characterised by abnormally decreased functional activity of the gonads, with retardation of growth and sexual development. "Osteopenia" refers to decreased calcification or density of bone. This is a term which encompasses all skeletal systems in which such a condition is noted.

"Osteoporosis" refers to a thinning of the bones with reduction in bone mass due to depletion of calcium and bone protein. Osteoporosis predisposes a person to fractures, which are often slow to heal and heal poorly. Unchecked osteoporosis can lead to changes in posture, physical abnormality, and decreased mobility.

"BPH (benign prostate hyperplasia)" is a nonmalignant enlargement of the prostate gland, and is the most common non-malignant proliferative abnormality found in any internal organ and the major cause of morbidity in the adult male. BPH occurs in over 75% of men over 50 years of age, reaching 88% prevalence by the ninth decade. BPH frequently results in a gradual squeezing of the portion of the urethra which traverses the prostate (prostatic urethra). This causes patients to experience a frequent urge to urinate because of incomplete emptying of the bladder and urgency of urination. The obstruction of urinary flow can also lead to a general lack of control over urination, including difficulty initiating urination when desired, as well as difficulty in preventing urinary flow because of the inability to empty urine from the bladder, a condition known as overflow urinary incontinence, which can lead to urinary obstruction and to urinary failure.

"Cognition" refers to the process of knowing, specifically the process of being aware, knowing, thinking, learning and judging. Cognition is related to the fields of psychology, linguistics, computer science, neuroscience, mathematics, ethology and philosophy. The term "mood" refers to a temper or state of the mind. As contemplated herein, alterations means any change for the positive or negative, in cognition and/or mood.

The term "depression" refers to an illness that involves the body, mood and thoughts, that affects the way a person eats, sleeps and the way one feels about oneself, and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

The term "hair loss", medically known as alopecia, refers to baldness as in the very common type of male-pattern baldness. Baldness typically begins with patch hair loss on the scalp and sometimes progresses to complete baldness and even loss of body hair. Hair loss affects both males and females.

"Anemia" refers to the condition of having less than the normal number of red blood cells or less than the normal quantity of hemoglobin in the blood. The oxygen-carrying capacity of the blood is, therefore, decreased. Persons with anemia may feel tired and fatigue easily, appear pale, develop palpitations and become; usually short of breath. Anemia is caused by four basic factors: a) hemorrhage (bleeding); b) hemolysis (excessive destruction of red blood cells); c) underproduction of red blood cells; and d) not enough normal hemoglobin. There are many forms of anemia, including aplastic anemia, benzene poisoning, Fanconi anemia, hemolytic disease of the newborn, hereditary spherocytosis, iron deficiency anemia, osteopetrosis, pernicious anemia, sickle cell disease, thalassemia, myelodysplastic syndrome, and a variety of bone marrow diseases. As contemplated herein, the SARM compounds of the present invention are useful in preventing and/or treating any one or more of the above-listed forms of anemia.

"Obesity" refers to the state of being well above one's normal weight. Traditionally, a person is considered to be obese if they are more than 20 percent over, their ideal weight. Obesity has been more precisely defined by the National Institute of Health (NIH) as a Body to Mass Index (BMI) of 30 or above. Obesity is often multifactorial, based on both genetic and behavioral factors. Overweight due to obesity is a significant contributor to health problems. It increases the risk of developing a number of diseases including: Type 2 (adult-onset) diabetes; high blood pressure (hypertension); stroke (cerebrovascular accident or CVA); heart attack (myocardial infarction or MI); heart failure (congestive heart failure); cancer (certain forms such as cancer of the prostate and cancer of the colon and rectum); gallstones and gallbladder disease (cholecystitis); Gout and gouty arthritis; osteoarthritis (degenerative arthritis) of the knees, hips, and the lower back; sleep apnea (failure to breath normally during sleep, lowering blood oxygen); and Pickwickian syndrome (obesity, red face, underventilation and drowsiness). As contemplated herein, the term "obesity" includes any one of the above-listed obesity-related conditions and diseases. Thus the SARM compounds of the present invention are useful in preventing and/or treating obesity and any one or more of the above-listed obesity-related conditions and diseases.

"Prostate cancer" is one of the most frequently occurring cancers among men in the United States, with hundreds of thousands of new cases diagnosed each year. Over sixty percent of newly diagnosed cases of prostate cancer are found to be pathologically advanced, with no cure and a dismal prognosis. One third of all men over 50 years of age have a latent form of prostate cancer that may be activated into the life-threatening clinical prostate cancer form. The frequency of latent prostatic tumors has been shown to increase substantially with each decade of life from the 50s (5.3–14%) to the 90s (40–80%). The number of people with latent prostate cancer is the same across all cultures, ethnic groups, and races, yet the frequency of clinically aggressive cancer is markedly different. This suggests that environmental factors may play a role in activating latent prostate cancer.

Pharmaceutical Compositions

The treatment methods of the present invention comprise, in one embodiment, administering a pharmaceutical preparation comprising the SARM compound and/or its analog, derivative, isomer, metabolite, pharmaceutically acceptable salt, pharmaceutical product, hydrate, N-oxide, prodrug, polymorph, crystal or any combination thereof; and a pharmaceutically acceptable carrier.

As used herein, "pharmaceutical composition" means a composition comprising an "effective amount" of the active ingredient, i.e. the SARM compound, together with a pharmaceutically acceptable carrier or diluent.

An "effective amount" as used herein refers to that amount which provides a therapeutic effect for a given condition and administration regimen. An "effective amount" of the SARM compounds as used herein can be in the range of 1–500 mg/day. In one embodiment the dosage is in the range of 1–100 mg/day. In another embodiment the dosage is in the range of 100–500 mg/day. In another embodiment the dosage is in a range of 45–60 mg/day. In another embodiment the dosage is in the range of 15–25 mg/day. In another embodiment the dosage is in the range of 55–65 mg/day. In another embodiment the dosage is in the range of 45–60 mg/day. [APPROPRIATE DOSAGES?] The SARM compounds can be administered daily, in single dosage forms containing the entire amount of daily dose, or can be administered daily in multiple doses such as twice daily or three times daily. The SARM compounds can also be administered intermittently, for example every other day, 3 days a week, four days a week, five days a week and the like.

As used herein, the term "treating" includes preventative as well as disorder remitative treatment. As used herein, the terms "reducing", "suppressing" and "inhibiting" have their commonly understood meaning of lessening or decreasing. As used herein, the term "facilitating" is giving its commonly understood meaning of increasing the rate. As used herein, the term "promoting" is given its commonly understood meaning of increasing. As used herein, the term "progression" means increasing in scope or severity, advancing, growing or becoming worse.

As used herein, the term "administering" refers to bringing a subject in contact with a SARM compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject. In one embodiment, the subject is a mammalian subject. In another embodiment, the subject is a human.

The pharmaceutical compositions containing the SARM agent can be administered to a subject by any method known to a person skilled in the art, such as parenterally, paracancerally, transmucosally, transdermally, intramuscularly, intravenously, intradermally, subcutaneously, intraperitonealy, intraventricularly, intracranially, intravaginally or intratumorally.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulstions, oils and the like. In one embodiment of the present invention, the SARM compounds are formulated in a capsule. In accordance with this embodiment, the compositions of the present invention comprise in addition to the SARM active compound and the inert carrier or diluent, a hard gelating capsule.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the SARM agents or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of SARM agent over a period of time.

In another embodiment, the active compound can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g: cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In one embodiment, the pharmaceutical compositions provided herein are controlled release compositions, i.e. compositions in which the SARM compound is released over a period of time after administration. Controlled or sustained release compositions include formulation in lipophilic depots (e.g. fatty acids, waxes, oils). In another embodiment, the composition is an immediate release composition, i.e. a composition in which all of the SARM compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115–138 (1984). Other controlled release systems are discussed in the review by Langer (Science 249:1527–1533 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the SARM agents or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the SARM agents or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the SARM will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

In one embodiment, the methods of the present invention comprise administering a SARM compound as the sole active ingredient. However, also encompassed within the scope of the present invention are methods of a) male contraception; b) treatment of a variety of hormone-related conditions, for example conditions associated with Androgen Decline in Aging Male (ADAM); c) treatment of conditions associated with Androgen Decline in Female (ADIF); d) treatment and/or prevention of acute and/or chronic muscular wasting conditions; e) preventing and/or treating dry eye conditions; f) oral androgen replacement therapy; g) decreasing the incidence of, halting or causing a regression of prostate cancer; andr h) inducing apoptosis in a cancer cell as disclosed herein, which comprise administering the SARM compounds in combination with one or more therapeutic agents. These agents include, but are not limited to: LHRH analogs, reversible antiandrogens, antiestrogens, anticancer drugs, 5-alpha reductase inhibitors, aromatase inhibitors, progestins, or agents acting through other nuclear hormone receptors.

Thus, in one embodiment, the present invention provides compositions and pharmaceutical compositions comprising a selective androgen receptor modulator compound, in combination with an LHRH analog. In another embodiment, the present invention provides compositions and pharmaceutical compositions comprising a selective androgen receptor modulator compound, in combination with a reversible antiandrogen. In another embodiment, the present invention provides compositions and pharmaceutical compositions comprising a selective androgen receptor modulator compound, in combination with an antiestrogen. In another embodiment, the present invention provides compositions and pharmaceutical compositions comprising a selective androgen receptor modulator compound, in combination with an anticancer drug. In another embodiment, the present invention provides compositions and pharmaceutical compositions comprising a selective androgen receptor modulator compound, in combination with a 5-alpha reductase inhibitor. In another embodiment, the present invention provides compositions and pharmaceutical compositions comprising a selective androgen receptor modulator compound, in combination with an aromatase inhibitor. In another embodiment, the present invention provides compositions and pharmaceutical compositions comprising a selective androgen receptor modulator compound, in combination with a progestin. In another embodiment, the present invention provides compositions and pharmaceutical compositions comprising a selective androgen receptor modulator compound, in combination with an agent acting through other nuclear hormone receptors.

It will be appreciated by a person skilled in the art that the present invention is not limited by what has been particularly shown and described hereinabove. Rather, the scope of the invention is defined by the claims that follow:

What is claimed is:

1. A selective androgen receptor modulator (SARM) compound represented by the structure of formula I:

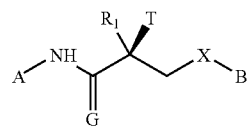

wherein

X is a bond, O, $CH_2$, NH, Se, PR, NO or NR;

G is O or S;

R1 is $CH_3$, $CH_2F$, $CHF_2$, $CF_3$, $CH_2CH_3$, or $CF_2CF_3$;

T is OH, OR, $NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

A is a ring selected from:

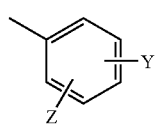 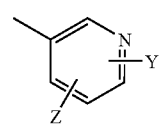 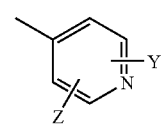

-continued

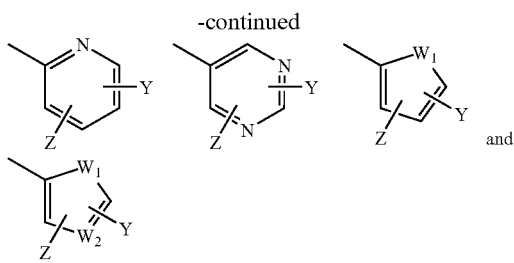

B is a ring selected from:

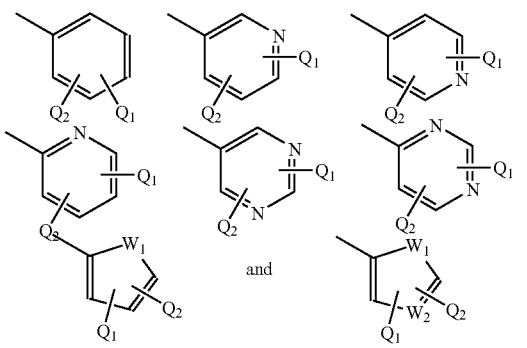

and wherein A and B cannot simultaneously be a benzene ring;
Z is NO$_2$, CN, COOH, COR, NHCOR or CONHR;
Y is CF$_3$, F, I, Br, Cl, CN, C(R)$_3$ or Sn(R)$_3$;
Q$_1$ and Q$_2$ are independently of each other a hydrogen, alkyl, F, Cl, Br, I, CF$_3$, CN C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR,

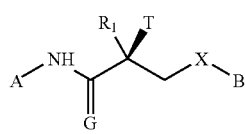

Q$_3$ and Q$_4$ are independently of each other a hydrogen, alkyl, F, Cl, Br, I, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;
W$_1$ is O, NH, NR, NO or S; and
W$_2$ is N or NO.

2. A selective androgen receptor modulator (SARM) compound represented by the structure of formula I:

$$A-NH-\underset{G}{\overset{R_1\ \ T}{\underset{|}{C}}}-X-B \qquad I$$

wherein
X is a bond, O, CH$_2$, NH, Se, PR, NO or NR;
G is O or S;
R$_1$ is CH$_3$, CH$_2$F, CHF$_2$, CF$_3$, CH$_2$CH$_3$, or CF$_2$CF$_3$;
T is OH, OR, NHCOCH$_3$, or NHCOR;

R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
A is a ring selected from:

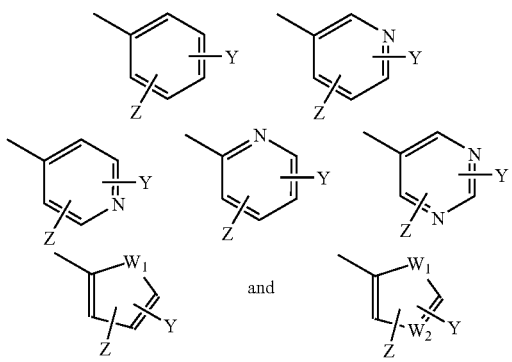

and

B is a ring selected from:

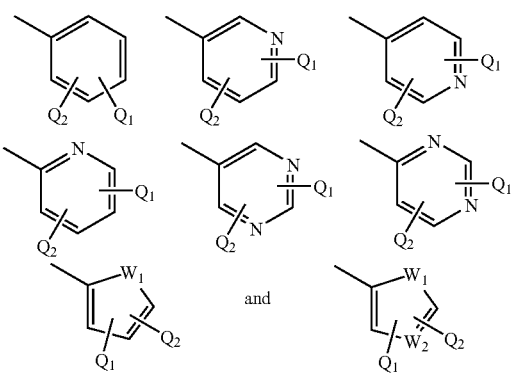

and wherein A and B cannot simultaneously be a benzene ring;
Z is NO$_2$, CN, COOH, COR, NHCOR or CONHR;
Y is CF$_3$, F, I, Br, Cl, CN, C(R)$_3$ or Sn(R)$_3$;
Q$_1$ and Q$_2$ are independently of each other a hydrogen, alkyl, F, Cl, Br, I, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR,

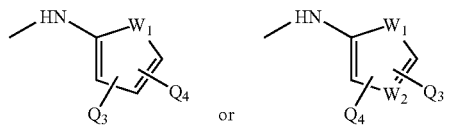

Q$_3$ and Q$_4$ are independently of each other a hydrogen, alkyl, F, Cl, Br, I, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;
W$_1$ is O, NH, NR, NO or S; and
W$_2$ is N or NO;

or its analog, derivative, isomer, metabolite, pharmaceutically acceptable salt, pharmaceutical product, hydrate, N-oxide, prodrug, polymorph, crystal or any combination thereof.

3. The selective androgen receptor modulator compound of claim 1, wherein X is O.

4. The selective androgen receptor modulator compound of claim 1, wherein G is O.

5. The selective androgen receptor modulator compound of claim 1, wherein T is OH.

6. The selective androgen receptor modulator compound of claim 1, wherein $R_1$ is $CH_3$.

7. The selective androgen receptor modulator compound of claim 1 wherein Z is $NO_2$.

8. The selective androgen receptor modulator compound of claim 1, wherein Z is CN.

9. The selective androgen receptor modulator compound of claim 1, wherein Y is $CF_3$.

10. The selective androgen receptor modulator-compound of claim 1, wherein $Q_1$ is $NHCOCH_3$.

11. The selective androgen receptor modulator compound of claim 1, wherein $Q_1$ is F.

12. The selective androgen receptor modulator compound of claim 1, represented by the structure of formula Ia:

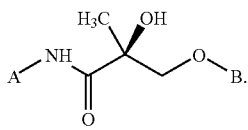

Ia

13. The selective androgen receptor modulator compound of claim 1, wherein A is

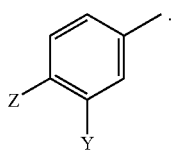

14. The selective androgen receptor modulator compound of claim 1, wherein A is

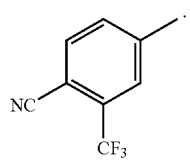

15. The selective androgen receptor modulator compound of claim 1, wherein A is

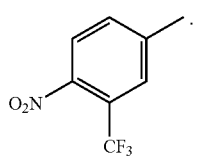

16. The selective androgen receptor modulator compound of claim 1, wherein A is

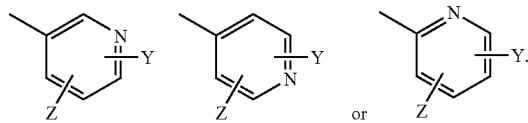

17. The selective androgen receptor modulator compound of claim 1, wherein B is

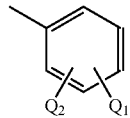

18. The selective androgen receptor modulator compound of claim 1, wherein B is

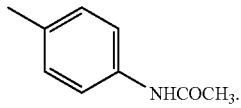

19. The selective androgen receptor modulator compound of claim 1, wherein B is

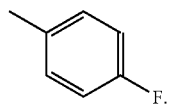

20. The selective androgen receptor modulator compound of claim 1, wherein B is

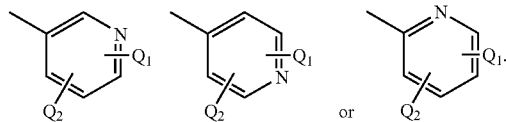

21. A composition comprising the selective androgen receptor modulator compound of claim 1 and/or its analog, derivative, isomer, metabolite, pharmaceutically acceptable salt, pharmaceutical product, hydrate, N-oxide, prodrug, polymorph, crystal or any combination thereof; and a suitable carrier or diluent.

22. A pharmaceutical composition comprising an effective amount of the selective androgen receptor modulator compound of claim 1 and/or its analog, derivative, isomer, metabolite, pharmaceutically acceptable salt, pharmaceutical product, hydrate, N-oxide, prodrug, polymorph, crystal or any combination thereof; and a pharmaceutically acceptable carrier, diluent or salt.

23. A selective androgen receptor modulator (SARM) compound represented by the structure of formula II:

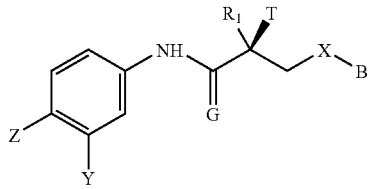

II wherein
X is a bond, O, $CH_2$, NH, Se, PR, NO or NR;
G is O or S;

$R_1$ is $CH_3$, $CH_2F$, $CHF_2$, $CF_3$, $CH_2CH_3$, or $CF_2CF_3$;
T is OH, OR, $NHCOCH_3$, or NHCOR;
R is alkyl, haloalkyl, dihaloalkyl, trihaloalkyl, $CH_2F$, $CHF_2$, $CF_3$, $CF_2CF_3$; aryl, phenyl, F, Cl, Br, I, alkenyl or OH;
B is a ring selected from:

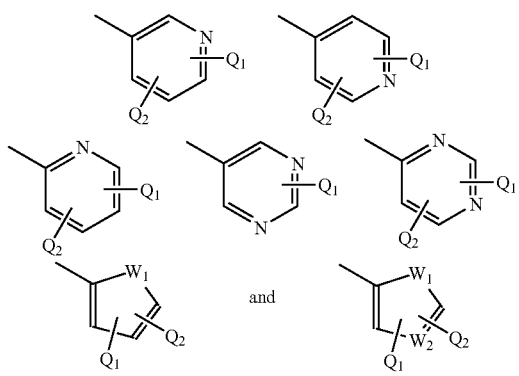

Z is $NO_2$, CN, COOH, COR, NHCOR or CONHR;
Y is $CF_3$, F, I, Br, Cl, CN, $C(R)_3$ or $Sn(R)_3$;
$Q_1$ and $Q_2$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR,

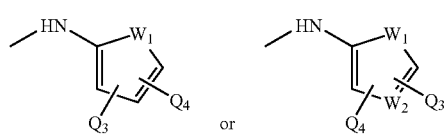

$Q_3$ and $Q_4$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$ or SR;
$W_1$ is O, NH, NR, NO or S; and
$W_2$ is N or NO.

24. A selective androgen receptor modulator (SARM) compound represented by the structure of formula II:

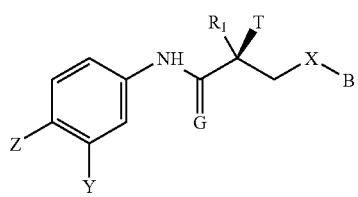

wherein
X is a bond, O, $CH_2$, NH, Se, PR, NO or NR;
G is O or S;
$R_1$ is $CH_3$, $CH_2F$, $CHF_2$, $CF_3$, $CH_2CH_3$, or $CF_2CF_3$;
T is OH, OR, $NHCOCH_3$, or NHCOR;

R is alkyl, haloalkyl, dihaloalkyl, trihaloalkyl, $CH_2F$, $CHF_2$, $CF_3$, $CF_2CF_3$; aryl, phenyl, F, Cl, Br, I, alkenyl or OH;
B is a ring selected from:

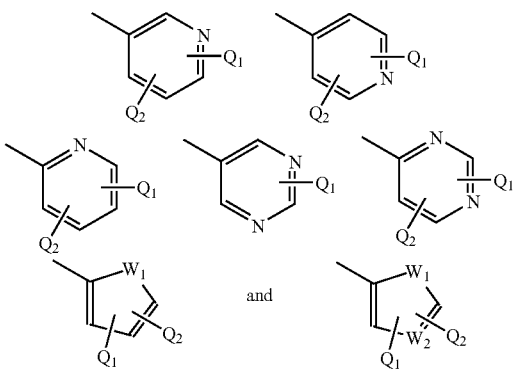

Z is $NO_2$, CN, COOH, COR, NHCOR or CONHR;
Y is $CF_3$, F, I, Br, Cl, CN, $C(R)_3$ or $Sn(R)_3$;
$Q_1$ and $Q_2$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR,

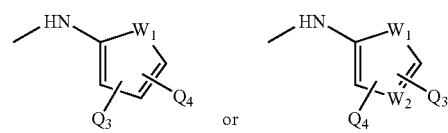

$Q_3$ and $Q_4$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$ or SR;
$W_1$ is O, NH, NR, NO or S; and
$W_2$ is N or NO;

or its analog, derivative, isomer, metabolite, pharmaceutically acceptable salt, pharmaceutical product, hydrate, N-oxide, prodrug, polymorph, crystal or any combination thereof.

25. The selective androgen receptor modulator compound of claim 23, wherein X is O.

26. The selective androgen receptor modulator compound of claim 23, wherein G is O.

27. The selective androgen receptor modulator compound of claim 23, wherein T is OH.

28. The selective androgen receptor modulator compound of claim 23, wherein $R_1$ is $CH_3$.

29. The selective androgen receptor modulator compound of claim 23 wherein Z is $NO_2$.

30. The selective androgen receptor modulator compound of claim 23 wherein Z is CN.

31. The selective androgen receptor modulator compound of claim 23 wherein Y is $CF_3$.

32. The selective androgen receptor modulator compound of claim 23, wherein $Q_1$ is $NHCOCH_3$.

33. The selective androgen receptor modulator compound of claim 23, wherein $Q_1$ is F.

34. The selective androgen receptor modulator compound of claim 23 represented by the structure of formula III:

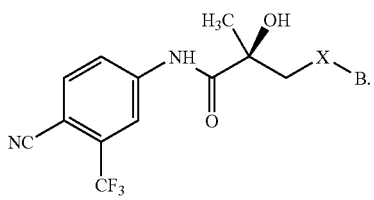

35. The selective androgen receptor modulator compound of claim 23 represented by the structure of formula IV:

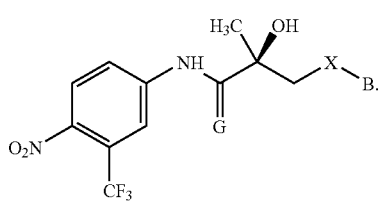

36. The selective androgen receptor modulator compound of claim 23 represented by the structure:

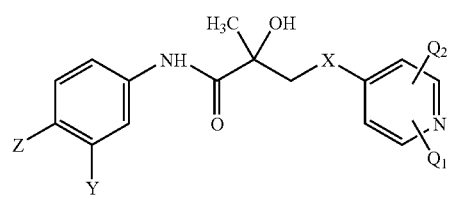

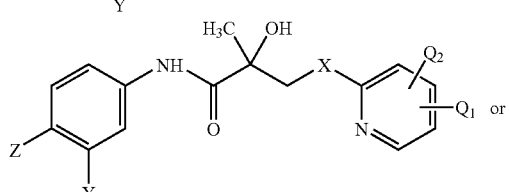

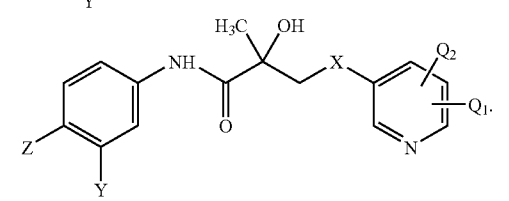 or

37. The selective androgen receptor modulator compound of claim 23 represented by the structure:

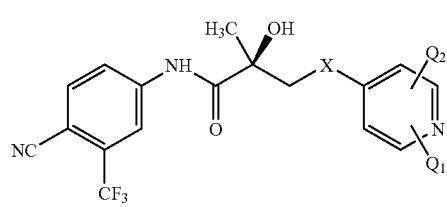

-continued

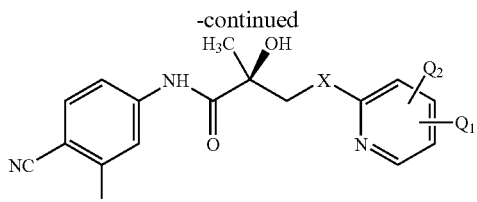

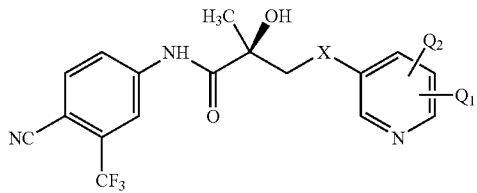

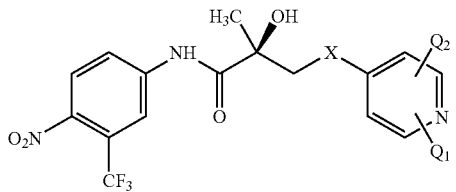

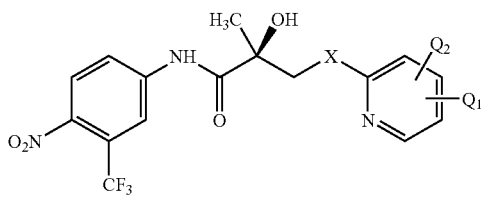 or

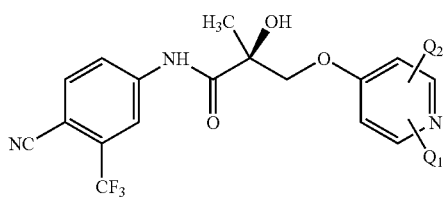

38. The selective androgen receptor modulator compound of claim 23 represented by the structure:

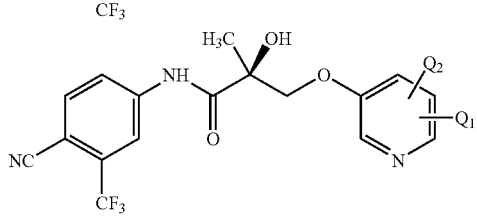

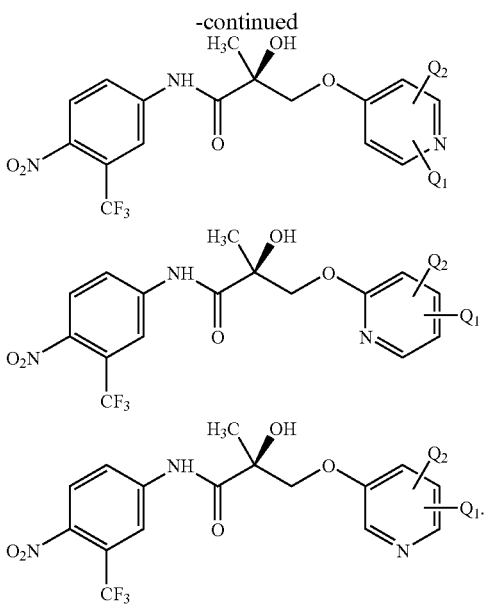

39. A composition comprising the selective androgen receptor modulator compound of claim 23 and/or its analog, derivative, isomer, metabolite, pharmaceutically acceptable salt, pharmaceutical product, hydrate, N-oxide, prodrug, polymorph, crystal or any combination thereof, and a suitable carrier or diluent.

40. A pharmaceutical composition comprising an effective amount of the selective androgen receptor modulator compound of claim 23 and/or its analog, derivative, isomer, metabolite, pharmaceutically acceptable salt, pharmaceutical product, hydrate, N-oxide, prodrug, polymorph, crystal or any combination thereof; and a pharmaceutically acceptable carrier, diluent or salt.

41. A selective androgen receptor modulator (SARM) compound represented by the structure of formula V:

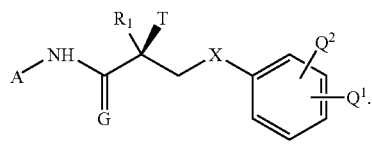

V wherein

X is a bond, O, $CH_2$, NH, Se, PR, NO or NR;

G is O or S;

$R_1$ is $CH_3$, $CH_2F$, $CHF_2$, $CF_3$, $CH_2CH_3$, or $CF_2CF_3$;

T is OH, OR, $NHCOCH_3$, or NHCOR;

R is alkyl, haloalkyl, dihaloalkyl, trihaloalkyl, $CH_2F$, $CHF_2$, $CF_3$, $CF_2CF_3$; aryl, phenyl, F, Cl, Br, I, alkenyl or OH;

A is a ring selected from:

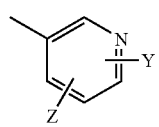 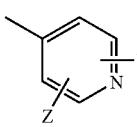 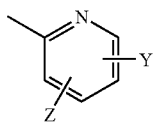

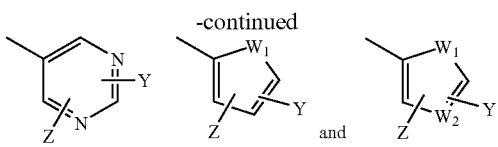

and

Z is $NO_2$, CN, COOH, COR, NHCOR or CONHR;

Y is $CF_3$, F, I, Br, Cl, CN, $C(R)_3$ or $Sn(R)_3$;

$Q_1$ and $Q_2$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR,

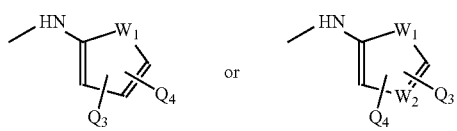

$Q_3$ and $Q_4$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$ or SR;

$W_1$ is O, NH, NR, NO or S; and $W_2$ is N or NO.

42. A selective androgen receptor modulator (SARM) compound represented by the structure of formula V:

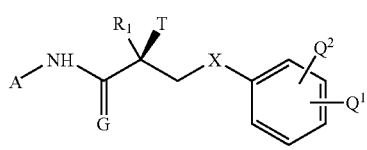

V wherein

X is a bond, O, $CH_2$, NH, Se, PR, NO or NR;

G is O or S;

$R_1$ is $CH_3$, $CH_2F$, $CHF_2$, $CF_3$, $CH_2CH_3$, or $CF_2CF_3$;

T is OH, OR, $NHCOCH_3$, or NHCOR;

R is alkyl, haloalkyl, dihaloalkyl, trihaloalkyl, $CH_2F$, $CHF_2$, $CF_3$, $CF_2CF_3$; aryl, phenyl, F, Cl, Br, I, alkenyl or OH;

A is a ring selected from:

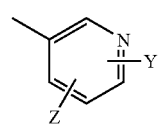

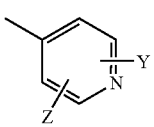 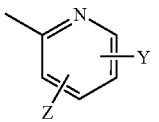 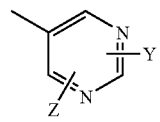

-continued

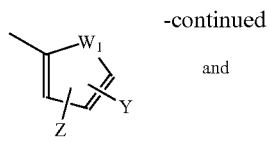
and

Z is NO₂, CN, COOH, COR, NHCOR or CONHR;
Y is CF₃, F, I, Br, Cl, CN, C(R)₃ or Sn(R)₃;
Q₁ and Q₂ are independently of each other a hydrogen, alkyl, F, Cl, Br, I, CF₃, CN, C(R)₃, Sn(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR,

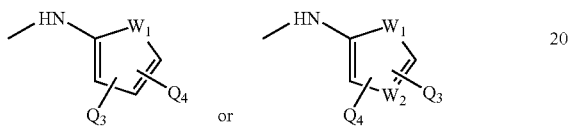

Q₃ and Q₄ are independently of each other a hydrogen, alkyl, F, Cl, Br, I, CF₃, CN, C(R)₃, Sn(R)₃, N(R)₃, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R or SR;
W₁ is O, NH, NR, NO or S; and
W₂ is N or NO;
or its analog, derivative, isomer, metabolite, pharmaceutically acceptable salt, pharmaceutical product, hydrate, N-oxide, prodrug, polymorph, crystal or any combination thereof.

43. The selective androgen receptor modulator compound of claim 41, wherein X is O.

44. The selective androgen receptor modulator compound of claim 41, wherein G is O.

45. The selective androgen receptor modulator compound of claim 41, wherein T is OH.

46. The selective androgen receptor modulator compound of claim 41, wherein R₁ is CH₃.

47. The selective androgen receptor modulator compound of claim 41, wherein Z is NO₂.

48. The selective androgen receptor modulator compound of claim 41, wherein Z is CN.

49. The selective androgen receptor modulator compound of claim 41, wherein Y is CF₃.

50. The selective androgen receptor modulator compound of claim 41, wherein Q₁ is NHCOCH₃.

51. The selective androgen receptor modulator compound of claim 41, wherein Q₁ is F.

52. The selective androgen receptor modulator compound of claim 41, represented by the structure of formula VI:

VI
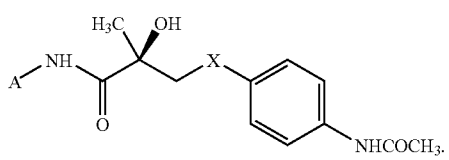

53. The selective androgen receptor modulator compound of claim 41, represented by the structure:

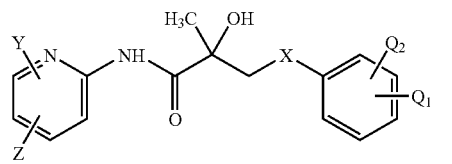

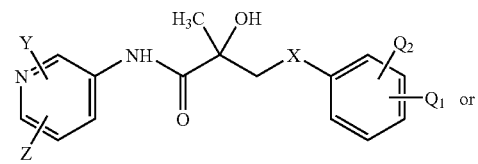 or

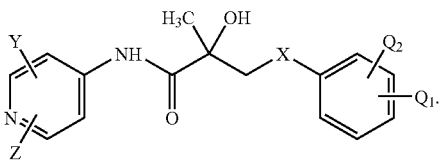

54. The selective androgen receptor modulator compound of claim 41, represented by the structure:

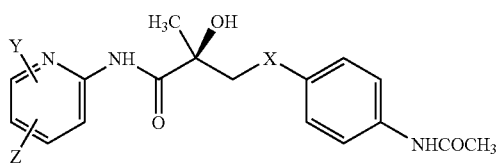

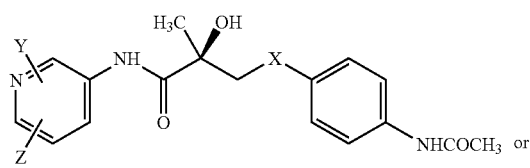 or

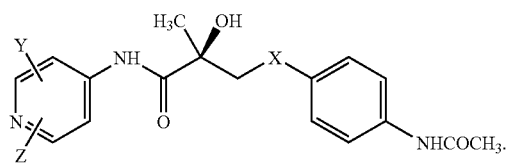

55. The selective androgen receptor modulator compound of claim 41, represented by the structure:

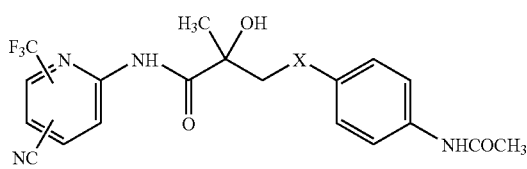

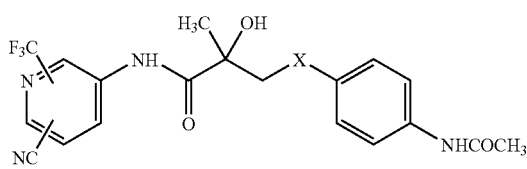

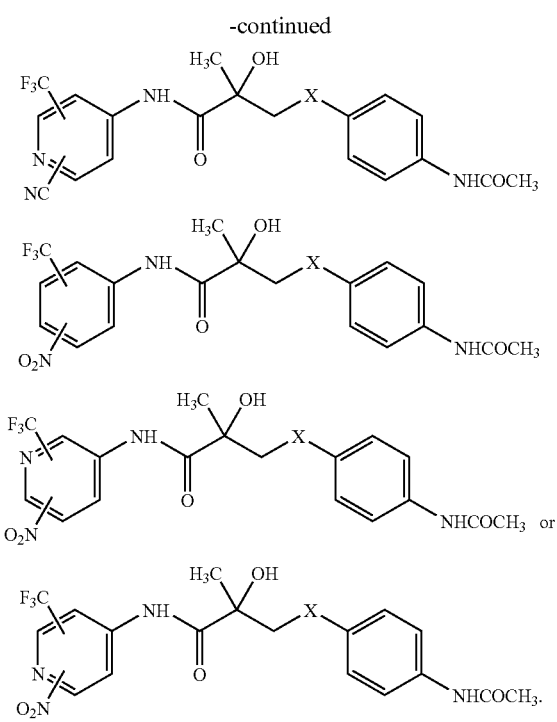

56. The selective androgen receptor modulator compound of claim 41, represented by the structure:

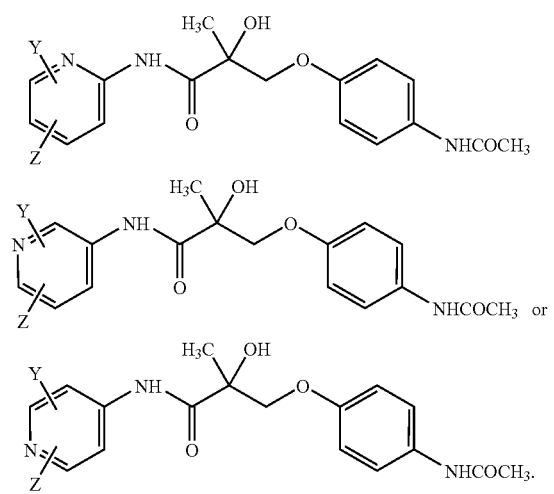

57. The selective androgen receptor modulator compound of claim 41, represented by the structure:

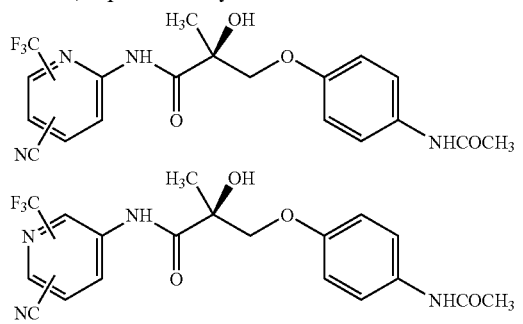

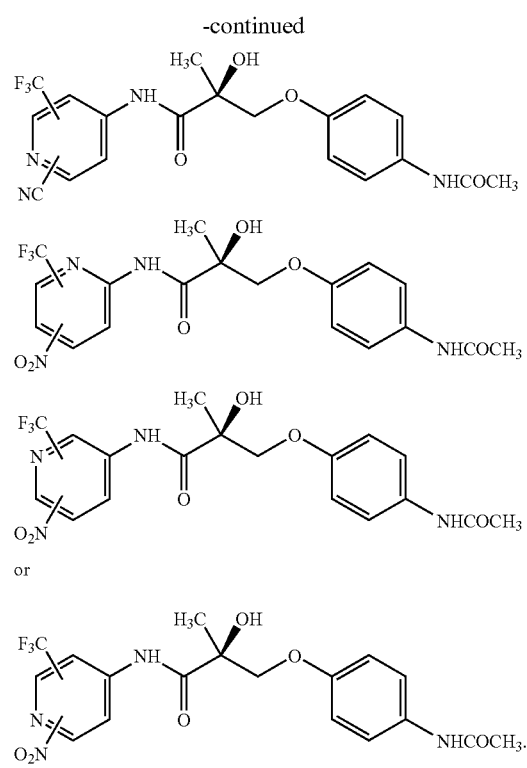

or

58. The selective androgen receptor modulator compound of claim 41, represented by the structure:

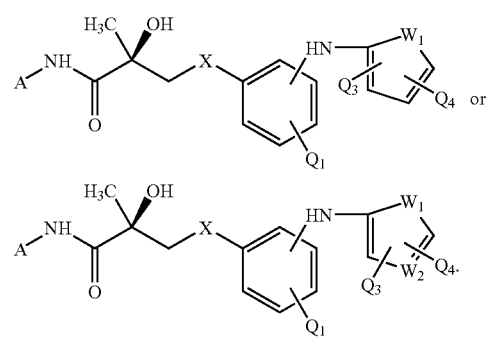

59. The selective androgen receptor modulator compound of claim 41, represented by the structure:

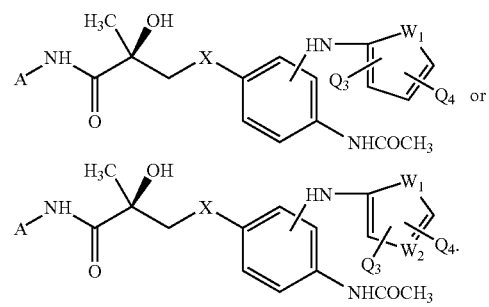

60. The selective androgen receptor modulator compound of claim 41, represented by the structure:

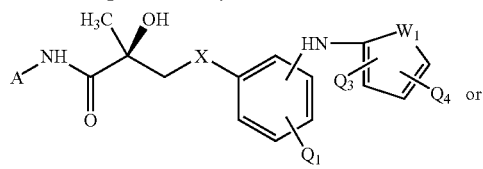

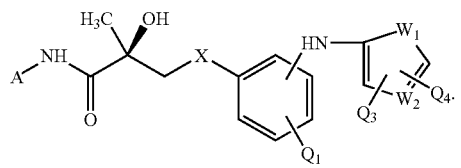

61. The selective androgen receptor modulator compound of claim 41, represented by the structure:

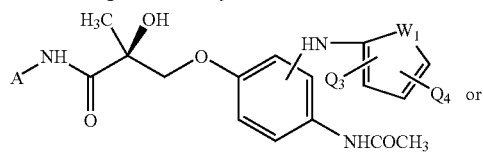

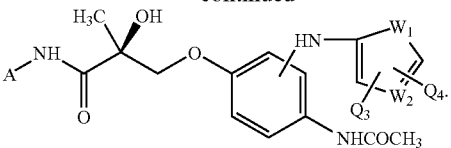

62. A composition comprising the selective androgen receptor modulator compound of claim 41 and/or its analog, derivative, isomer, metabolite, pharmaceutically acceptable salt, pharmaceutical product, hydrate, N-oxide, prodrug, polymorph, crystal or any combination thereof; and a suitable carrier or diluent.

63. A pharmaceutical composition comprising an effective amount of the selective androgen receptor modulator compound of claim 41 and/or its analog, derivative, isomer, metabolite, pharmaceutically acceptable salt, pharmaceutical product, hydrate, N-oxide, prodrug, polymorph, crystal or any combination thereof; and a pharmaceutically acceptable carrier, diluent or salt.

* * * * *